(12) United States Patent
Isobe et al.

(10) Patent No.: US 8,044,056 B2
(45) Date of Patent: Oct. 25, 2011

(54) ADENINE COMPOUND

(75) Inventors: Yoshiaki Isobe, Osaka (JP); Tomoaki Nakamura, Osaka (JP)

(73) Assignees: Dainippon Sumitomo Pharma Co., Ltd., Osaka (JP); AstraZeneca Aktiebolag, Sodertalje (SE)

( * ) Notice: Subject to any disclaimer, the term of this patent is extended or adjusted under 35 U.S.C. 154(b) by 0 days.

(21) Appl. No.: 12/531,867

(22) PCT Filed: Mar. 19, 2008

(86) PCT No.: PCT/JP2008/055088
§ 371 (c)(1),
(2), (4) Date: Sep. 17, 2009

(87) PCT Pub. No.: WO2008/114819
PCT Pub. Date: Sep. 25, 2008

(65) Prior Publication Data
US 2010/0099870 A1   Apr. 22, 2010

(30) Foreign Application Priority Data

Mar. 20, 2007 (JP) ................................. 2007-071711

(51) Int. Cl.
| C07D 473/18 | (2006.01) |
| A61K 31/522 | (2006.01) |
| C07D 241/08 | (2006.01) |
| C07D 241/04 | (2006.01) |
| A61P 37/08 | (2006.01) |
| A61P 11/06 | (2006.01) |
| A61P 37/06 | (2006.01) |

(52) U.S. Cl. ........... 514/252.16; 514/263.22; 514/263.2; 544/276; 544/385; 544/403

(58) Field of Classification Search ............... 514/263.2, 514/263.22, 252.16; 544/276
See application file for complete search history.

(56) References Cited

U.S. PATENT DOCUMENTS

| 4,179,562 A | 12/1979 | Ponsford |
| 4,689,338 A | 8/1987 | Gerster |
| 4,698,348 A | 10/1987 | Gerster |
| 4,714,701 A | 12/1987 | Beauchamp |
| 4,912,112 A | 3/1990 | Seydel et al. |
| 5,736,549 A | 4/1998 | Beasley et al. |
| 5,994,361 A | 11/1999 | Penney et al. |
| 6,028,076 A | 2/2000 | Hirota et al. |
| 6,110,923 A | 8/2000 | Ely |
| 6,329,381 B1 | 12/2001 | Kurimoto et al. |
| 6,376,501 B1 | 4/2002 | Isobe et al. |
| 6,448,236 B1 | 9/2002 | Monaghan |
| 6,458,798 B1 | 10/2002 | Fujita et al. |
| 6,630,478 B2 | 10/2003 | Diamond et al. |
| 6,887,880 B2 | 5/2005 | Levy et al. |
| 6,951,866 B2 | 10/2005 | Fujita et al. |
| 7,157,465 B2 | 1/2007 | Isobe et al. |
| 7,521,454 B2 | 4/2009 | Isobe et al. |
| 7,642,350 B2 * | 1/2010 | Pryde .............................. 544/61 |
| 7,691,877 B2 | 4/2010 | Jones et al. |
| 2002/0040032 A1 | 4/2002 | Glasky et al. |
| 2002/0128264 A1 | 9/2002 | Taylor et al. |
| 2003/0144283 A1 | 7/2003 | Coleman et al. |
| 2003/0191086 A1 | 10/2003 | Hanus et al. |
| 2003/0212092 A1 | 11/2003 | Heppner et al. |
| 2004/0019048 A1 | 1/2004 | Crooks et al. |
| 2004/0204438 A1 | 10/2004 | Crooks et al. |
| 2004/0214192 A1 | 10/2004 | Hashida et al. |
| 2004/0229897 A1 | 11/2004 | Crooks et al. |
| 2005/0054590 A1 | 3/2005 | Averett |
| 2005/0119273 A1 | 6/2005 | Lipford et al. |
| 2006/0052403 A1 | 3/2006 | Isobe et al. |

(Continued)

FOREIGN PATENT DOCUMENTS

CA         1220148         4/1987

(Continued)

OTHER PUBLICATIONS

Isobe, Y., et al., "Synthesis and Structure-Activity Relationships of 2-Substituted-8-hydroxyadenine Derivatives as Orally Avaliable Interferon Inducers without Emetic Side Effects," Bioorg. & Medicinal Chem., vol. 11, pp. 3641-3647 (2003).

Hirota, K., et al., "Discovery of 8-Hydroxyadenines as a Novel Type of Interferon Inducer," J. Med. Chem., vol. 45, pp. 5419-5422 (2002).

Kurimoto, A., et al., "Synthesis and Structure-Activity Relationshps of 2-Amino-8-hydroxyadenines as Orally Active Interferon Inducing Agents," Bioorg. Medicinal Chem., vol. 11, pp. 5501-5508 (2003).

Kurimoto, A., et al., "Synthesis and evaluation of 2-substituted 8-hydroxyadenines as potent interferon inducers with improved oral bioavailabilities," Bioorg. & Medicinal Chem., vol. 12, pp. 1091-1099 (2004).

(Continued)

Primary Examiner — Mark Berch
(74) Attorney, Agent, or Firm — Morgan, Lewis & Bockius LLP

(57) ABSTRACT

A novel adenine compound represented by the formula (1):

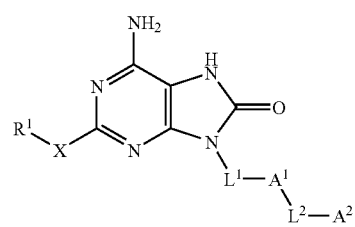

[wherein $R^1$ is substituted or unsubstituted alkyl, etc., X is oxygen, etc., $A^1$ is 4- to 8-membered substituted or unsubstituted saturated nitrogen-containing heterocycle containing 1 to 2 hetero atom(s) selected from 1 to 2 nitrogen(s), 0 to 1 oxygen and 0 to 1 sulfur, etc., $A^2$ is substituted or unsubstituted 6- to 10-membered aryl, etc., $L^1$ and $L^2$ are independently a straight chain or branched chain alkylene, etc.], or a pharmaceutically acceptable salt thereof, which is useful as a medicament.

10 Claims, No Drawings

U.S. PATENT DOCUMENTS

| | | | |
|---|---|---|---|
| 2006/0252774 A1 | 11/2006 | Vatner et al. | |
| 2007/0190071 A1* | 8/2007 | Kurimoto et al. | 424/184.1 |
| 2007/0225303 A1 | 9/2007 | Ogita et al. | |
| 2007/0249638 A1 | 10/2007 | Giorgio et al. | |
| 2008/0008682 A1* | 1/2008 | Chong et al. | 424/85.6 |
| 2008/0269240 A1* | 10/2008 | Hashimoto et al. | 514/252.16 |
| 2008/0300244 A1* | 12/2008 | Bonnert et al. | 514/232.5 |
| 2009/0047249 A1* | 2/2009 | Graupe et al. | 424/85.6 |
| 2009/0082332 A1* | 3/2009 | Abbot et al. | 514/210.21 |
| 2009/0099216 A1* | 4/2009 | Millichip et al. | 514/263.38 |
| 2009/0105212 A1* | 4/2009 | Isobe et al. | 514/210.21 |
| 2009/0118263 A1* | 5/2009 | Hashimoto et al. | 514/218 |
| 2009/0131458 A1* | 5/2009 | Lazarides et al. | 514/263.23 |
| 2009/0143400 A1* | 6/2009 | McInally et al. | 514/252.16 |
| 2009/0192153 A1* | 7/2009 | Hashimoto et al. | 514/234.2 |
| 2009/0202484 A1* | 8/2009 | Chong et al. | 424/85.6 |
| 2009/0209524 A1 | 8/2009 | Bennett et al. | |
| 2009/0281075 A1 | 11/2009 | Roughton et al. | |
| 2009/0324551 A1* | 12/2009 | Carson et al. | 424/93.4 |
| 2009/0325877 A1* | 12/2009 | Grunt et al. | 514/12 |
| 2010/0075995 A1* | 3/2010 | Biggadike et al. | 514/263.22 |
| 2010/0087443 A1* | 4/2010 | Bonnert et al. | 514/252.16 |
| 2010/0093998 A1* | 4/2010 | Isobe et al. | 540/575 |
| 2010/0099870 A1* | 4/2010 | Isobe et al. | 544/276 |
| 2010/0120799 A1* | 5/2010 | Lazarides et al. | 514/263.23 |
| 2010/0130491 A1 | 5/2010 | Bonnert et al. | |
| 2010/0240623 A1* | 9/2010 | Cook et al. | 514/171 |
| 2010/0280001 A1 | 11/2010 | Bonnert et al. | |
| 2010/0298364 A1 | 11/2010 | Bennett et al. | |
| 2011/0028715 A1 | 2/2011 | Isobe et al. | |
| 2011/0046369 A1 | 2/2011 | Hashimoto et al. | |
| 2011/0054168 A1 | 3/2011 | Kurimoto et al. | |

FOREIGN PATENT DOCUMENTS

| | | |
|---|---|---|
| CN | 101239980 | 8/2008 |
| EP | 1386923 | 2/2004 |
| EP | 1908480 A1 | 4/2008 |
| GB | 1375162 | 11/1974 |
| JP | 08-165292 | 6/1996 |
| JP | 347422/1997 | 11/1997 |
| JP | 367449/1997 | 12/1997 |
| JP | 367451/1997 | 12/1997 |
| JP | 10-501533 | 2/1998 |
| JP | 10-507171 | 7/1998 |
| JP | 11-180981 | 7/1999 |
| JP | 11-180982 | 7/1999 |
| JP | 11-193282 A | 7/1999 |
| JP | 2000-159767 | 6/2000 |
| JP | 2004137157 A | 5/2004 |
| JP | 2005-089334 | 4/2005 |
| WO | WO 95/35297 | 12/1995 |
| WO | WO 96/11200 | 4/1996 |
| WO | WO-98/01448 A1 | 1/1998 |
| WO | WO-99/28321 A1 | 6/1999 |
| WO | WO 99/50249 | 10/1999 |
| WO | WO 00/12487 | 3/2000 |
| WO | WO 00/76519 | 12/2000 |
| WO | WO 01/27131 | 4/2001 |
| WO | WO 02/04449 | 1/2002 |
| WO | WO 02/04451 | 1/2002 |
| WO | WO 02/40481 | 5/2002 |
| WO | WO 02/085905 | 10/2002 |
| WO | WO 03/011864 | 2/2003 |
| WO | WO 2004/011481 | 2/2004 |
| WO | WO-2004/029054 A1 | 4/2004 |
| WO | WO 2004/075865 | 9/2004 |
| WO | WO 2004/087049 | 10/2004 |
| WO | WO-2005/092892 A1 | 10/2005 |
| WO | WO-2005/092893 A1 | 10/2005 |
| WO | WO 2006/029115 | 3/2006 |
| WO | WO 2006/091394 | 8/2006 |
| WO | WO-2006/117670 A1 | 11/2006 |
| WO | WO-2007/024707 A2 | 3/2007 |
| WO | WO 2007/031726 | 3/2007 |
| WO | WO 2007/034173 | 3/2007 |
| WO | WO 2007/034817 | 3/2007 |
| WO | WO 2007/034881 | 3/2007 |
| WO | WO 2007/034882 | 3/2007 |
| WO | WO 2007/034916 | 3/2007 |
| WO | WO 2007/034917 | 3/2007 |
| WO | WO 2007/093901 | 8/2007 |
| WO | WO 2008004948 A1 * | 1/2008 |
| WO | WO 2008/114006 | 9/2008 |
| WO | WO 2008/114008 | 9/2008 |
| WO | WO 2008/114817 | 9/2008 |
| WO | WO 2008/135791 | 11/2008 |
| WO | WO 2009/005687 | 1/2009 |
| WO | WO 2009/062059 | 5/2009 |
| WO | WO 2009/067081 | 5/2009 |
| WO | WO 2009/078798 | 6/2009 |
| WO | WO 2009/091031 | 7/2009 |
| WO | WO 2009/091032 | 7/2009 |
| WO | WO 2010018131 A1 * | 2/2010 |
| WO | WO 2010018134 A1 * | 2/2010 |
| WO | WO 2010/033074 | 3/2010 |
| WO | WO 2010/133882 | 11/2010 |

OTHER PUBLICATIONS

Kurimoto, A., et al., "Prodrugs of 9-Benzyl-8-hydroxy-2-(2-hydroxyethylthio)adenine: Potent Interferon Inducing Agents in Monkeys," Chem. Pharm. Bull., vol. 52, No. 4, pp. 466-469 (2004).

Isobe, Y., et al., "Synthesis and Biological Evaluation of Novel 9-Substituted-8-Hydroxyadenine Derivatives as Potent Interferon Inducers," J. Med. Chem., vol. 49, pp. 2088-2095 (2006).

Holy, A., et al., "9-(Aminoalkyl)-8-Hydroxyadenines: Preparation, Mechanism of Formation and Use in Affinity Chromatography of S-Adenosyl-L-Homocysteine Hydrolase," Institute of Org. Chem. and Biochem., Czech Chem. Commun., vol. 51, No. 2, pp. 459-477 (1986).

IPRP of PCT/JP2008/055088—English Translation.

"Asthma" (MDAdvice.com) retrieved on Jun. 24, 2010 from the interne (URL: http://www.mdadvice.com/topics/asthma/info/1.htm).

"Chronic obstructive pulmonary disease"(AllRefer.com Health) retrieved on Jun. 24, 2010 from the internet (URL: http://health.allrefer.com/health/chronic-obstructive-pulmonary-disease-prevention.html).

"Respiratory experts call for global approach to treat chronic diseases" (Feb. 13, 2007) retrieved on Jun. 24, 2010 from the internet (URL: http://www.medwire-news.md/48/64443/Respiratory/Respiratory_experts_call_for_global_approach_to_treat_chronic_disease.html).

Aoki et al., "Weekly dosing of AZD8848/DSP-3025, A novel TLR7 agonist antedrug, demonstrates a prolonged period of control against markers of pulmonary inflammation in an alergen challenge model in the mouse" ATS International Conference, New Orleans, May 2010.

Bell et al., "AZD8848/DSP-3025, A novel potent TLR7 agonist antedrug, demonstrates negligible systemic activity and a prolonged period of control after cessation of weekly dosing in a brown norway rat ovalbumin challenge model" ATS International Conference, New Orleans, May 2010.

Biffen et al., "Biological activity of a novel TLR7 agonist antedrug for the treatment of allergic diseases," ATS International Conference, New Orleans, May 2010.

Chavarot et al., "Synthesis of an adenine-pyridinaldoxime-acridine conjugate for recognition of abasic site lesions in DNA," Tetrahedron, 53(40): 13749-13756 (1997).

Drazen, "Surgery for emphysema—Not for everyone" New England Journal of Medicine, 345(15): 1126-1128 (2001).

Dvorakova et al., "Synthesis of 2'-aminomethyl derivatives of N-(2-(phosphonomethoxy)ethyl) nucleotide analogues as potential antiviral agents," J. Med. Chem., 39(17): 3263-3268 (1996).

Falco et al., "2,4-Diaminopyrimidines as antimalarials. i.1 5-aryloxyl and 5-alkoxyl derivatives," Journal of the American Chemical Society 73(8): 3753-3758 (1951).

Fridkin, "Vancomycin-intermediate and -resistant staphylococcus aureus: what the infectious disease specialist needs to know," Clinical Infectious diseases, Society for Healthcare Epidemiology of America, 32: 108-115 (2001).

Ikeda et al., "AZD8848/DSP-3025, A novel potent TLR7 agonist antedrug, demonstrates efficacy against airway obstruction and other inflammatory endpoints in guinea pig models of rhinitis and asthma with acute and weekly dosing" ATS International Conference, New Orleans, May 2010.

Itahara et al., "Control of liquid-crystalline properties by base pairing of adenine and thymine," ChemPhysChem, 3(4): 378-379 (2002).

Korc, "Pathways for aberrant angiogenesis in pancreatic cancer," Molecular Cancer, Biomed Central, 2(8): 1-8 (2003).

Krueger et al., "Tilorone hydrochloride: An orally active antiviral agent," Science, 169: 1213-1214 (1970).

Kurimoto et al., "Synthesis and biological evaluation of 8-oxoadenine derivatives as Toll-like Receptor 7 agonists introducing the antedrug concept," J. Med. Chem., 53: 2964-2972 (2010).

Laino, "In small study, imaging detects lung damage in people exposed to secondhand smoke," Oncology Times, 30(2): 15 (Jan. 25, 2008).

Lee et al., "Activation of anti-hepatitis C 1-17,21-22 virus responses via Toll-like receptor 7," Proc. Natl. Acad. Sci. USA, 103(6):1828-1833 (2006).

Lee et al., "Molecular basis for the immunostimulatory activity of guanine nucleoside analogs: Activation of Toll-like receptor 7," Proc. Natl. Acad. Sci. USA, 100(11):6646-6651 (2003).

Matsui et al., "Mechanisms of inhibition of type-2 cytokines by novel TLR7 agonist antedrugs," ATS International Conference, New Orleans, May 2010.

Mayer et al., "Tilorone hydrochloride: Mode of acton," Science, 169:1214-1215 (1970).

McInally "Identification and pharmacology of novel TLR7 agonist antedrugs," RSC BMSC Inflammation meeting, Nov. 18, 2010.

McInally et al., "Identification of a novel TLR7 agonist antedrug," EFMC-ISMC 2010, 21st International Symposium on Medicinal Chemistry, Brussels, Belgium, Sep. 5-9, 2010.

Mogulkoc et al., "Pulmonary function in idiopathic pulmonary fibrosis and referral for lung transplantation," American Journal of Respiratory and Critical Care Medicine, 164(1): 103-108 (2001).

Nichol et al., "Stimulation of murine interferon by a substituted pyrimidine," Antimicrobial Agents and Chemotherapy, 9(3): 433-439 (1976).

Palmer et al., "Highly drug-resistant HIV-1 clinical isolates are cross-resistant to many antiretroviral compounds in current clinical development," AIDS, Lippincott Williams & Wilkins, 13(6): 661-667 (1999).

Reiter et al., "Cytokine induction in mice by the immunomodulator imiquimod," Journal of Leukocyte Biology, 55: 234-240 (1994).

Spassova et al., "Synthesis of N-(3-Azido-2-hydroxypropyl), N-(3-Phthalimido-2-hydroxypropyl) and N-(3-Amino-2-hydroxypropyl) Derivatives of Heterocyclic Bases," Collection of Czechoslovak chemical Communications, 59(5): 1153-1174 (1994).

Stringfellow et al., "Antiviral and interferon-inducing properties of 1,5-diamino anthraquinones," Antimicrobial Agents and Chemotherapy, 15(1): 111-118 (1979).

Tarkoy et al., "Nucleic-acid analogues with constraint conformational flexibility in the sugar-phosphate backbone ('Bicyclo-DNA')," Helvetica Chimica Acta, 76(1): 481-510 (1993).

Tojo et al., "Synthesis and biological evaluation of a novel TLR7 agonist with an antedrug strategy," EFMC-ISMC 2010, 21st International Symposium on Medicinal Chemistry, Brussels, Belgium, Sep. 5-9, 2010.

Yoshimoto et al., "Correlation analysis of Baker's studies on enzyme inhibition. 2. Chymotrypsin, trypsin, thymidine phosphorylase, uridine phosphorylase, thymidylate synthetase, cytosine nucleoside deaminase, dihydrofolate reductase, malate dehydrogenase, glutamate dehydrogenase, lactate dehydrogenase, and glyceraldehyde-phosphate dehydrogenase," Journal of Medicinal Chemistry, 19(1): 71-98 (1976).

Zalutsky, "Targeted radiotherapy of brain tumors," British Journal of Cancer, 90: 1469-1473 (2004).

* cited by examiner

ADENINE COMPOUND

This Application is the National Phase Under 35 U.S.C. §371 of PCT International Application No. PCT/JP2008/055088 which has an International filing date of Mar. 19, 2008, which claims priority to JP 2007-071711 filed on Mar. 20, 2007.

CROSS-REFERENCE TO RELATED APPLICATIONS

NAMES OF PARTIES TO A JOINT RESEARCH AGREEMENT

The subject matter claimed in this application was made as a result of activities undertaken within the scope of a joint research agreement dated Dec. 19, 2003, between AstraZeneca AB and Sumitomo Pharmaceuticals Co., Ltd. All of the rights and obligations of Sumitomo Pharmaceuticals Co., Ltd. as defined in the joint research agreement between Astra-Zeneca AB and Sumitomo Pharmaceuticals Co., Ltd. were assumed by Dainippon Sumitomo Pharma Co., Ltd., a company created by the merger of Dainippon Pharmaceuticals Co., Ltd. and Sumitomo Pharmaceuticals Co., Ltd. effective Oct 3, 2005.

TECHNICAL FIELD

The present invention relates to a novel adenine compound being useful as a therapeutic and/or preventive agent for allergic diseases, viral diseases, cancers, etc.

BACKGROUND ART

In case that foreign substances including bacteria, virus or parasite invade living organisms, immune systems exist in order to exclude said substances. In acquired immune systems, antigen processing by antigen presenting cells such as dendritic cells (DCs) is carried out when the foreign substances invade, and naive Th cells functionally differentiate via interactions of DCs/Th cells into Th1 cells or Th2 cells which play a central role of immune response in vivo. It is believed that immune diseases are developed by one-way deflection of immuno-balance of Th1 cells or Th2 cells in this process.

Specifically, cytokine such as interleukin-4 (IL-4) and interleukin-5 (IL-5) secreted by Th2 cells is secreted in an excess amount within the body of patients with allergic diseases, and a compound inhibiting immune response of Th2 cells may be expected to be a therapeutic agent for allergic diseases. Also, a compound enhancing immune response of Th1 cells such as interferon α-inducing activity may be expected to be a therapeutic or preventive agent for viral diseases, cancers, etc.

In the meantime, it was believed until recently that natural immune system was caused by nonspecific phagocytosis, but it was proved that Toll-like receptor (TLR) exists and principal parts of natural immunity activation are carried out via TLR. Moreover, since TLR recognizes a ligand to induce inflammatory cytokine such as IL-12, TNF, etc. and IL-12 differentiates and induces naive T cell to Th1 cell, a ligand of TLR may be expected to have a function as a Th1/Th2 differentiation controlling agent and to be useful for treatment or prevention of immune diseases. Actually, it is known that Th2 cell predominates in patients with asthma, atopic dermatitis, etc., and asthma-targeted clinical trials are carried out for DNA (CpG DNA) derived from microorganism, which is TLR9 agonist. Additionally, it is known that TLR7/8 agonist imidazoquinoline derivative (see Patent Document 1) also shows producing inhibitory activity of Th2 cytokine, interleukin-4 (IL-4) and interleukin-5 (IL-5), and it is actually effective for allergic diseases in animal models.

Meanwhile, compounds described in, for example, Patent Documents 2 to 4 are known as compounds with adenine skeletons which are effective for immune diseases such as viral diseases and allergic diseases.

Patent Document 1: U.S. Pat. No. 4,689,338
Patent Document 2: WO 98/01448
Patent Document 3: WO 99/28321
Patent Document 4: WO 04/029054

DISCLOSURE OF INVENTION

Problems to be solved by the invention are to provide a TLR activator, more particularly, a novel adenine compound acting as a TLR7 activator, and further to provide an immune response-regulating agent comprising the same as the active ingredient, for example, a therapeutic or preventive agent for allergic diseases such as asthma, COPD, allergic rhinitis, allergic conjunctivitis or atopic dermatitis, viral diseases such as hepatitis B, hepatitis C, HIV or HPV, bacterial infectious diseases, cancers or dermatitis, etc.

The present inventors have intensively studied in order to obtain a therapeutic or preventive agent for immune diseases such as allergic diseases, viral diseases or cancers with excellent TLR activating effect, and have found the novel adenine compounds of the present invention. In other words, the compounds of the present invention are effective as a therapeutic or preventive agent for allergic diseases, viral diseases, cancers, etc.

The present invention has been accomplished based on the above findings.

By the present invention, it has become possible to provide a novel adenine compound being useful as a therapeutic or preventive agent for allergic diseases, viral diseases, cancers, etc.

Specifically, the present invention relates to the following inventions.

[1] An adenine compound of the formula (1):

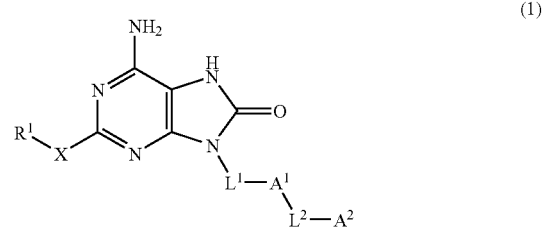

[wherein $R^1$ is a halogen atom, a substituted or unsubstituted $C_{1-12}$ alkyl group, a substituted or unsubstituted $C_{2-10}$ alkenyl group, a substituted or unsubstituted $C_{2-10}$ alkynyl group, a substituted or unsubstituted $C_{3-8}$ cycloalkyl group, a substituted or unsubstituted 6- to 10-membered aryl group, or a substituted or unsubstituted 5- to 10-membered heteroaryl group, X is an oxygen atom, a sulfur atom, $NR^2$ ($R^2$ is a hydrogen atom or a $C_{1-6}$ alkyl group), SO, $SO_2$ or a single bond (when $R^1$ is a halogen atom, then X is a single bond), $A^1$ is a 4- to 8-membered substituted or unsubstituted, saturated nitrogen-containing heterocycle or unsaturated non-aromatic nitrogen-containing heterocycle, said group containing 1 to 2 heteroatom(s) selected from 1 to 2 nitrogen atom(s), 0 to 1 oxygen atom and 0 to 1 sulfur atom, $A^2$ is a substituted or unsubstituted 6- to 10-membered aromatic carbocycle (aryl group) or a substituted or unsubstituted 5- to 10-membered aromatic heterocycle (heteroaryl group), $L^1$ and $L^2$ are independently a $C_{1-12}$ alkylene, a $C_{2-12}$ alkenylene, or a single bond, and any 1 to 3 methylene group(s) in said alkylene or alkenylene may be replaced by an oxygen atom, a sulfur atom, $NR^3$ ($R^3$ is a hydrogen atom or a $C_{1-6}$ alkyl group), SO, $SO_2$, or a carbonyl group], or a pharmaceutically acceptable salt thereof;

[2] The adenine compound according to [1], wherein when the alkyl group, the alkenyl group and the alkynyl group for $R^1$ are substituted, those groups are substituted by 1 or more groups selected from the following (a) to (c):

(a) a halogen atom, a hydroxy group, a carboxyl group, a mercapto group, an oxo group, a $C_{1-6}$ haloalkyl group and a $C_{1-6}$ haloalkoxy group;

(b) a $C_{1-6}$ alkoxy group, a $C_{2-6}$ alkylcarbonyl group, a $C_{2-6}$ alkoxycarbonyl group, a $C_{1-6}$ alkylsulfonyl group, a $C_{1-6}$ alkylsulfinyl group, a $C_{2-6}$ alkylcarbonyloxy group and a $C_{1-6}$ alkylthio group (the groups of this group may optionally and independently be substituted by 1 or more groups selected from a halogen atom, a hydroxy group, a carboxyl group, a $C_{1-6}$ alkoxy group, a $C_{2-6}$ alkoxycarbonyl group, an amino group being optionally substituted by the same or different 1 or 2 of $C_{1-6}$ alkyl group(s), a carbamoyl group being optionally substituted by the same or different 1 or 2 of $C_{1-6}$ alkyl group(s), a sulfamoyl group being optionally substituted by the same or different 1 to 2 of $C_{1-6}$ alkyl group(s), and a $C_{1-6}$ alkylsulfonyl group);

(c) an amino group, a carbamoyl group and a sulfamoyl group (these 3 groups may optionally be substituted by 1 or 2 groups selected from the following (k), (l) and (m)), a 3- to 8-membered cycloalkyl group, a 3- to 8-membered cycloalkoxy group and a 4- to 8-membered saturated heterocyclic group (these 3 groups may optionally be substituted by 1 or more groups selected from the following (d), (e) and (f))), and a 6- to 10-membered aryl group, a 5- to 10-membered heteroaryl group, a 6- to 10-membered aryloxy group and a 5- to 10-membered heteroaryloxy group (these 4 groups may optionally be substituted by 1 or more groups selected from the following (g), (h), (i) and (j)), When the cycloalkyl group for $R^1$ is substituted, it is substituted by 1 or more groups selected from the following (d) to (f):

(d) a halogen atom, a hydroxy group, a carboxyl group, a mercapto group, an oxo group, a cyano group, a nitro group, a $C_{1-6}$ haloalkyl group, and a $C_{1-6}$ haloalkoxy group;

(e) a $C_{1-6}$ alkyl group, a $C_{1-6}$ alkoxy group, a $C_{2-6}$ alkenyl group, a $C_{2-6}$ alkynyl group, a $C_{2-6}$ alkylcarbonyl group, a $C_{2-6}$ alkoxycarbonyl group, a $C_{1-6}$ alkylsulfonyl group and a $C_{1-6}$ alkylthio group (the groups of this group may optionally and independently be substituted by 1 or more groups selected from a halogen atom, a hydroxy group, a carboxyl group, a $C_{1-6}$ alkoxy group, a $C_{2-6}$ alkoxycarbonyl group, an amino group being optionally substituted by the same or different 1 or 2 of $C_{1-6}$ alkyl group(s), a carbamoyl group being optionally substituted by the same or different 1 or 2 of $C_{1-6}$ alkyl group(s), a sulfamoyl group being optionally substituted by the same or different 1 or 2 of $C_{1-6}$ alkyl group(s), and a $C_{1-6}$ alkylsulfonyl group);

(f) an amino group, a carbamoyl group and a sulfamoyl group (these 3 groups may optionally be substituted by 1 to 2 groups selected from the following (k), (l) and (m)), a 6- to 10-membered aryl group and a 5- to 10-membered heteroaryl group (these 2 groups may optionally be substituted by 1 or more groups selected from the following (g), (h), (i) and (j)), When the aryl group and heteroaryl group for $R^1$ is substituted, these groups are substituted by 1 or more groups selected from the following (g) to (j):

(g) a halogen atom, a hydroxy group, a mercapto group, a cyano group, a nitro group, a $C_{1-6}$ haloalkyl group, and a $C_{1-6}$ haloalkoxy group;

(h) a $C_{1-6}$ alkyl group, a $C_{1-6}$ alkoxy group, a $C_{2-6}$ alkenyl group, a $C_{2-6}$ alkynyl group, a $C_{2-6}$ alkylcarbonyl group, a $C_{2-6}$ alkoxycarbonyl group, and a $C_{1-6}$ alkylthio group (the groups of this group may optionally and independently be substituted by 1 or more groups selected from a halogen atom, a hydroxy group, a carboxyl group, a $C_{1-6}$ alkoxy group, a $C_{2-6}$ alkoxycarbonyl group, an amino group being optionally substituted by the same or different of 1 or 2 $C_{1-6}$ alkyl group(s), a carbamoyl group being optionally substituted by the same or different 1 to 2 of $C_{1-6}$ alkyl group(s), a sulfamoyl group being optionally substituted by the same or different 1 to 2 of $C_{1-6}$ alkyl group(s), and a $C_{1-6}$ alkylsulfonyl group);

(i) a 3- to 8-membered cycloalkyl group and a 4- to 8-membered saturated heterocyclic group (the groups of this group may optionally and independently be substituted by 1 or more groups selected from a halogen atom, a hydroxy group, a carboxyl group, a $C_{1-6}$ alkyl group and a $C_{1-6}$ alkoxy group);

(j) an amino group, a carbamoyl group, and a sulfamoyl group (the groups of this group may optionally be substituted by 1 to 2 groups selected from the following (k), (l) and (m));

(k) a $C_{1-6}$ alkyl group, a $C_{2-6}$ alkenyl group, a $C_{2-6}$ alkynyl group, a $C_{2-6}$ alkylcarbonyl group, a $C_{2-6}$ alkoxycarbonyl group, a $C_{1-6}$ alkylsulfonyl group, a $C_{1-6}$ alkylsulfinyl group, a 3- to 8-membered cycloalkyl group, a 3- to 8-membered cycloalkylcarbonyl group, a 3- to 8-membered cycloalkoxycarbonyl group, a 3- to 8-membered cycloalkyl-sulfonyl group, and a 3- to 8-membered cycloalkylsulfinyl group (the groups of this group may optionally be substituted by 1 or more groups selected from a halogen atom, a hydroxy group, a carboxyl group, a $C_{1-6}$ alkoxy group and a $C_{2-6}$ alkoxycarbonyl group);

(l) a 6- to 10-membered aryl group, a 6- to 10-membered arylcarbonyl group, a 6- to 10-membered aryloxycarbonyl group, a 6- to 10-membered arylsulfonyl group, a 6- to 10-membered arylsulfinyl group, a 5- to 10-membered heteroaryl group, a 5- to 10-membered heteroarylcarbonyl group, a 5- to 10-membered heteroaryloxycarbonyl group, a 5- to 10-membered heteroarylsulfonyl group, and a 5- to 10-membered heteroarylsulfinyl group (the groups of this group may optionally be substituted by a halogen atom, a hydroxy group, a mercapto group, a cyano group, a nitro group, a carboxyl group, a $C_{1-6}$ alkyl group, a $C_{1-6}$ alkoxy group, a $C_{2-6}$ alkoxycarbonyl group, or a $C_{1-6}$ alkylthio group);

(m) a group where 2 substituents combine together with a nitrogen atom to form a 4- to 8-membered nitrogen-containing saturated heterocycle containing 1 to 4 heteroatom(s) selected from 1 to 3 nitrogen atom(s), 0 to 1 oxygen atom, and 0 to 1 sulfur atom (said nitrogen-containing saturated heterocycle may optionally be substituted by the same or different 1 or more groups selected from a halogen atom, a hydroxy group, a carboxyl group, a $C_{1-6}$ alkyl group, a $C_{1-6}$ alkoxy group, a $C_{2-6}$ alkoxycarbonyl group and a $C_{2-6}$ alkylcarbonyl group on any carbon atoms or nitrogen atoms, as long as it may be kept in chemically stable state), When the 4- to 8-membered nitrogen-containing heterocycle for $A^1$ is substituted, it is substituted by 1 or more group(s) independently selected from the group consisting of a halogen atom, a hydroxy group, an oxo group, a $C_{1-6}$ alkyl group, a $C_{1-6}$ alkoxy group, a $C_{2-6}$ alkyl-carbonyl group, and a $C_{2-6}$ alkoxycarbonyl group;

When the 6- to 10-membered aromatic carbocycle (aryl group) and the 5- to 10-membered aromatic heterocycle (heteroaryl group) for $A^2$ are substituted, they are substituted by 1 or more group(s) independently selected from the group consisting of the following (g') to (i');

(g') a halogen atom, a hydroxy group, a mercapto group, a cyano group, a nitro group, a $C_{1-6}$ haloalkyl group, and a $C_{1-6}$ haloalkoxy group;

(h') a $C_{1-6}$ alkyl group, a $C_{1-6}$ alkoxy group, a $C_{2-6}$ alkylcarbonyl group, a $C_{1-6}$ alkylsulfonyl group, and a $C_{1-6}$ alkylthio group [the groups of this group may optionally be substituted by the same or different 1 or more groups selected from a halogen atom, a hydroxy group, a $C_{1-6}$ alkoxy group, a $C_{1-6}$ alkylsulfonyl group, an amino group, a carbamoyl group and a sulfamoyl group (the above amino, carbamoyl and sulfamoyl groups may optionally be substituted by 1 to 2 groups selected from the following (j') and (k'))];

(i') an amino group, a carbamoyl group, and a sulfamoyl group (the groups of this group may optionally be substituted by 1 or 2 groups selected from the following (j') and (k'));

(j') a $C_{1-6}$ alkyl group, a $C_{2-6}$ alkylcarbonyl group, a $C_{1-6}$ alkylsulfonyl group, a $C_{1-6}$ alkylsulfinyl group, a 3- to 8-membered cycloalkyl group, a 3- to 8-membered cycloalkylcarbonyl group, a 3- to 8-membered cycloalkoxycarbonyl group, a 3- to 8-membered cyclo-alkylsulfonyl group, and a 3- to 8-membered cycloalkylsulfinyl group (the groups of this group may optionally and independently be substituted by 1 or more groups selected from a halogen atom, a hydroxy group, a $C_{1-6}$ alkyl group and a $C_{1-6}$ alkoxy group);

(k') a group where 2 substituents combine together with a nitrogen atom to form a 4- to 8-membered nitrogen-containing saturated heterocycle containing 1 to 4 heteroatom(s) selected from 1 to 3 nitrogen atom(s), 0 to 1 oxygen atom, and 0 to 1 sulfur atom (said nitrogen-containing saturated heterocycle may optionally be substituted by 1 or more groups selected from a halogen atom, a hydroxy group, a $C_{1-6}$ alkyl group, a $C_{1-6}$ alkoxy group and a $C_{2-6}$ alkylcarbonyl group on any carbon atoms or nitrogen atoms, as long as it may be kept in chemically stable state),
or a pharmaceutically acceptable salt thereof;

[3] The adenine compound according to [1] or [2], or a pharmaceutically acceptable salt thereof, wherein in the formula (1), $A^1$ is pyrrolidine, piperidine, azetidine, piperazine, morpholine, thiomorpholine, thiomorpholin-1-oxide, or thiomorpholine-1,1-dioxide, these groups being either substituted or unsubstituted;

[4] The adenine compound according to any one of [1] or [3], or a pharmaceutically acceptable salt thereof, wherein in the formula (1), $A^2$ is a phenyl group, a pyridyl group, a furyl group, an imidazolyl group or a thienyl group, these groups being either substituted or unsubstituted;

[5] The adenine compound according to any one of [1] or [4], or a pharmaceutically acceptable salt thereof, wherein in the formula (1), $A^1$ is pyrrolidine, piperidine or piperazine, and $A^2$ is a substituted or unsubstituted phenyl group or a substituted or unsubstituted pyridyl group;

[6] The adenine compound according to any one of [1] or [5], or a pharmaceutically acceptable salt thereof, wherein in the formula (1), $L^1$ is a group of the following formula:

$(CH_2)_n$—$(Y^4)_m$—$(CH_2)_l$

[in which n and l are independently an integer of 0 to 5, m is 0 or 1, and $Y^4$ is an oxygen atom or $NR^3$ ($R^3$ is the same as defined in the above [1])], $L^2$ is a single bond, an oxygen atom, a carbonyl group, a $C_{1-10}$ straight chain or branched chain alkylene, a $C_{2-10}$ straight chain or branched chain alkenylene, or a group of the following formula:

$(CH_2)_a$—$(CO)_p$—$(CH_2)_q$—$(NR^3)_r$—$(CH_2)_t$—$(O)_u$

[in which $R^3$ is the same as defined in the above $R^3$, a, t and q are independently an integer of 0 to 4, p, r and u are independently 0 or 1, provided that when r and u are 1, then t is 2 or more];

[7] The adenine compound according to any one of [1] to [5], or a pharmaceutically acceptable salt thereof, wherein in the formula (1), $L^1$ is a $C_{2-8}$ straight chain or branched chain alkylene, and $L^2$ is a single bond, an oxygen atom, a carbonyl group, a $C_{1-6}$ straight chain or branched chain alkylene or a $C_{2-6}$ straight chain or branched chain alkenylene;

[8] The adenine compound according to any one of [1] to [7] or a pharmaceutically acceptable salt thereof, wherein $R^3$ is a hydrogen atom or a $C_{1-4}$ alkyl group;

[9] The adenine compound according to [1] or a pharmaceutically acceptable salt thereof, which is selected from the following compounds:
2-butoxy-7,8-dihydro-9-(3-[4-(4-methylbenzyl)piperazin-1-yl]-propyl)-8-oxoadenine,
9-(3-[4-benzylpiperidin-1-yl]propyl)-2-butoxy-7,8-dihydro-8-oxoadenine,
2-butoxy-7,8-dihydro-9-(3-[4-(4-fluorobenzoyl)piperidine-1-yl]-propyl)-8-oxoadenine,
2-butoxy-9-(3-[4-cinnamylpiperazin-1-yl]propyl)-7,8-dihydro-8-oxoadenine,
9-(7-[4-(4-acetylphenyl)piperazin-1-yl]heptyl)-2-butoxy-7,8-dihydro-8-oxoadenine,
2-butoxy-7,8-dihydro-9-(7-[4-(4-pyridyl)piperazin-1-yl]heptyl)-8-oxoadenine,
2-butoxy-9-(7-[4-(4-chloro-2-methylphenoxy)piperazin-1-yl]-heptyl)-7,8-dihydro-8-oxoadenine,
2-butoxy-7,8-dihydro-9-(7-[4-(4-methoxyphenyl)piperazin-1-yl]-heptyl)-8-oxoadenine,
6-amino-9-[2-(1-benzylpiperidin-4-yl)ethyl]-2-(2-methoxyethoxy)-7,9-dihydropurin-8-one,
6-amino-9-{2-[1-(4-dimethylaminomethylbenzyl)piperidin-4-yl]-ethyl}-2-(2-methoxyethoxy)-7,9-dihydropurin-8-one,
9-[1-(3-{N-benzyl,N-methylamino}propyl)piperidin-4-yl]methyl-2-butoxy-7,8-dihydro-8-oxoadenine,
2-butoxy-7,8-dihydro-9-{1-[3-(N-2-phenoxyethyl-N-methyl-amino)propyl]piperidin-4-ylmethyl}-8-oxoadenine,
2-butoxy-7,8-dihydro-9-[7-(4-{2-[N-methyl-N-benzyl]aminoethyl}-piperazin-1-yl)pentyl]-8-oxoadenine,
2-butoxy-7,8-dihydro-9-[7-(4-{2-[N-methyl-N-benzyl]aminoethyl}-piperazin-1-yl)heptyl]-8-oxoadenine,
2-butoxy-7,8-dihydro-9-(7-{4-[2-phenoxyethyl]piperazin-1-yl}-heptyl)-8-oxoadenine,
9-(3-[2-benzyl-4-methyl-piperazin-1-yl]propyl)-2-butoxy-7,8-dihydro-8-oxoadenine,
9-(3-[3-benzyl-4-methyl-piperazin-1-yl]propyl)-2-butoxy-7,8-dihydro-8-oxoadenine,
2-butoxy-7,8-dihydro-9-(3-{1-(2-phenoxyethyl)piperidin-4-yl}-propyl)-8-oxoadenine,
2-butoxy-7,8-dihydro-9-[3-{1-(3-phenylpropyl)piperidin}-4-yl]-propyl)-8-oxoadenine;

[10] A pharmaceutical composition comprising as the active ingredient an adenine compound as set forth in any one of [1] to [9] or a pharmaceutically acceptable salt thereof;

[11] An agent for increasing TLR7 activity comprising as the active ingredient an adenine compound as set forth in any one of [1] to [9], or a pharmaceutically acceptable salt thereof;

[12] An immune response regulating agent comprising as the active ingredient an adenine compound as set forth in any one of [1] to [9], or a pharmaceutically acceptable salt thereof;

[13] A therapeutic or preventive agent for allergic diseases, viral diseases or cancers, which comprises as the active ingredient an adenine compound as set forth in any one of [1] to [9], or a pharmaceutically acceptable salt thereof;

[14] A therapeutic or preventive agent for asthma, COPD, allergic rhinitis, allergic conjunctivitis, atopic dermatitis, cancer, hepatitis B, hepatitis C, HIV, HPV, bacterial infectious disease or dermatitis, which comprises as the active ingredient an adenine compound as set forth in any one of [1] to [9], or a pharmaceutically acceptable salt thereof;

The embodiments of the present invention are explained in detail below.

The "halogen atom" as used in the present description includes fluorine, chlorine, bromine or iodine, preferably fluorine or chlorine.

The "alkyl group" includes a $C_{1-12}$ straight chain or branched chain alkyl group, particularly, methyl, ethyl, propyl, 1-methylethyl, butyl, 2-methylpropyl, 1-methylpropyl, 1,1-dimethylethyl, pentyl, 3-methylbutyl, 2-methylbutyl, 2,2-dimethylpropyl, 1-ethylpropyl, 1,1-dimethylpropyl, hexyl, 4-methylpentyl, 3-methylpentyl, 2-methylpentyl, 1-methylpentyl, 3,3-dimethylbutyl, 2,2-dimethylbutyl, 1,1-dimethyl-butyl, 1,2-dimethylbutyl, heptyl, 1-methylhexyl, 1-ethylpentyl, octyl, 1-methylheptyl, 2-ethylhexyl, nonyl, or decyl. Preferable one is a $C_{1-6}$ alkyl group, more preferably, a $C_{1-4}$ alkyl group.

The "alkenyl group" includes a $C_{2-10}$ straight chain or branched chain alkenyl group, particularly, ethenyl, propenyl, 1-methylethenyl, butenyl, 2-methylpropenyl, 1-methylpropenyl, pentenyl, 3-methyl-butenyl, 2-methylbutenyl, 1-ethylpropenyl, hexenyl, 4-methylpentenyl, 3-methylpentenyl, 2-methylpentenyl, 1-methylpentenyl, 3,3-dimethyl-butenyl, 1,2-dimethylbutenyl, heptenyl, 1-methylhexenyl, 1-ethylpentenyl, octenyl, 1-methylheptenyl, 2-ethylhexenyl, nonenyl, or decenyl. Preferable one is a $C_{2-6}$ alkenyl group, more preferably a $C_{2-4}$ alkenyl group.

The "alkynyl group" includes a $C_{2-10}$ straight chain or branched chain alkynyl group, particularly, ethynyl, propynyl, butynyl, pentynyl, 3-methylbutynyl, hexynyl, 4-methylpentynyl, 3-methylpentynyl, 3,3-dimethylbutynyl, heptynyl, octynyl, 3-methylheptynyl, 3-ethylhexynyl, nonynyl, or decynyl. Preferable one is a $C_{2-6}$ alkynyl group, more preferably a $C_{2-4}$ alkynyl group.

The "cycloalkyl group" includes a 3- to 8-membered monocyclic cycloalkyl group, particularly, cyclopropyl, cyclobutyl, cyclopentyl, cyclohexyl, cycloheptyl or cyclooctyl.

The "cycloalkoxy group" includes a 3- to 8-membered monocyclic cycloalkoxy group, particularly, cyclopropyloxy, cyclobutyloxy, cyclopentyloxy, cyclohexyloxy, cycloheptyloxy or cyclooctyloxy.

The "aryl group" includes a 6- to 10-membered aryl group, particularly, phenyl, 1-naphthyl or 2-naphthyl. Preferable one is phenyl.

The "heteroaryl group" includes a 5- to 10-membered mono- or bi-cyclic heteroaryl group containing 1 to 4 heteroatom(s) selected from 0 to 3 nitrogen atom(s), 0 to 1 oxygen atom and 0 to 1 sulfur atom, particularly, furyl, thienyl, pyrrolyl, pyridyl, indolyl, isoindolyl, quinolyl, isoquinolyl, pyrazolyl, imidazolyl, pyrimidinyl, pyrazinyl, pyridazinyl, thiazolyl, or oxazolyl. The binding position of these groups is not necessarily specified, and the groups may bind on any carbon atoms or nitrogen atoms, as long as it may be kept in chemically stable state. Preferable one is a 5- or 6-membered monocyclic heteroaryl group.

The "saturated heterocyclic group" includes a 4- to 10-membered mono- or bi-cyclic saturated heterocyclic group containing 1 to 4 heteroatom(s) selected from 0 to 3 nitrogen atom(s), 0 to 1 oxygen atom and 0 to 1 sulfur atom, wherein said sulfur atom may optionally be substituted by 1 or 2 oxygen atom(s). Examples thereof are azetidinyl, pyrrolidinyl, piperidinyl, piperazinyl, morpholinyl, thiomorpholinyl, 1-oxothiomorpholinyl, 1,1-dioxothiomorpholinyl, tetrahydrofuranyl, or oxazolidinyl. The binding position of these groups is not necessarily specified, and these substituent(s) may bind on any carbon atoms or nitrogen atoms, as long as it may be kept in chemically stable state. Preferable one is a 4- to 8-membered monocyclic saturated heterocyclic group.

The "alkylene" includes a $C_{1-12}$ straight chain or branched chain alkylene, particularly, methylene, ethylene, trimethylene, tetramethylene, pentamethylene, hexamethylene, heptamethylene, octamethylene, nonamethylene, decamethylene, 1-methylmethylene, 1-ethylmethylene, 1-propylmethylene, 1-methylethylene, 2-methylethylene, 1-methyltrimethylene, 2-methyltrimethylene, 2-methyltetramethylene, or 3-methylpentamethylene. The preferable one is a $C_{1-10}$, more preferable one is a $C_{1-8}$, and the further preferable one is a $C_{1-6}$ straight chain or branched chain alkylene.

The "haloalkyl group" includes a $C_{1-6}$ alkyl group being substituted by 1 to 5 of the same or different halogen atom(s), particularly, trifluoromethyl, 2,2,2-trifluoroethyl, 2,2-difluoroethyl, or pentafluoroethyl.

The "alkoxy group" includes a $C_{1-10}$ straight chain or branched chain alkoxy group, particularly, methoxy, ethoxy, propoxy, 1-methyl-ethoxy, butoxy, 2-methylpropoxy, 1-methylpropoxy, 1,1-dimethylethoxy, pentoxy, 3-methylbutoxy, 2-methylbutoxy, 2,2-dimethylpropoxy, 1-ethylpropoxy, 1,1-dimethylpropoxy, hexyloxy, 4-methylpentyloxy, 3-methylpentyloxy, 2-methylpentyloxy, 1-methylpentyloxy, 3,3-dimethyl-butoxy, 2,2-dimethylbutoxy, 1,1-dimethylbutoxy, 1,2-dimethylbutoxy, heptyloxy, 1-methylhexyloxy, 1-ethylpentyloxy, octyloxy, 1-methyl-heptyloxy, 2-ethylhexyloxy, nonyloxy, or decyloxy. Preferable one is a $C_{1-6}$ alkoxy group, more preferably, a $C_{1-4}$ alkoxy group.

The "haloalkoxy group" includes a $C_{1-6}$ alkoxy group being substituted by 1 to 5 of the same or different halogen atom(s), particularly, trifluoromethoxy, 2,2,2-trifluoroethoxy, 2,2-difluoroethoxy, 2-fluoroethoxy, or pentafluoroethoxy.

The "alkyl" in the "alkylthio group", the "alkylcarbonyl group", the "alkylcarbonyloxy group", the "alkylsulfonyl group" or the "alkylsulfinyl group" includes the same one as the above-mentioned alkyl group.

The "alkylthio group" includes a $C_{1-10}$ straight chain or branched chain alkylthio group, preferably $C_{1-6}$ alkylthio group, more preferably a $C_{1-4}$ alkylthio group.

The "alkylcarbonyl group" includes a $C_{2-11}$ straight chain or branched chain alkylcarbonyl group, preferably a $C_{2-6}$ alkylcarbonyl group, more preferably a $C_{2-5}$ alkylcarbonyl group.

The "alkylcarbonyloxy group" includes a $C_{2-11}$ straight chain or branched chain alkylcarbonyloxy group, preferably a $C_{2-6}$ alkylcarbonyl-oxy group, more preferably a $C_{2-5}$ alkylcarbonyloxy group.

The "alkylsulfonyl group" includes a $C_{1-10}$ straight chain or branched chain alkylsulfonyl group, preferably a $C_{1-6}$ alkylsulfonyl group, more preferably a $C_{1-4}$ alkylsulfonyl group.

The "alkylsulfinyl group" includes a $C_{1-10}$ straight chain or branched chain alkylsulfinyl group, preferably a $C_{1-6}$ alkylsulfinyl group, more preferably a $C_{1-4}$ alkylsulfinyl group.

The "alkoxy" in the "alkoxycarbonyl group" includes the same as the alkoxy group as mentioned above. Namely, the "alkoxycarbonyl group" includes a $C_{2-11}$ straight chain or branched chain alkoxycarbonyl group, preferably a $C_{2-6}$ alkoxycarbonyl group, more preferably a $C_{2-5}$ alkoxycarbonyl group.

The "cycloalkyl" in the "cycloalkylcarbonyl group", the "cyclo-alkylcarbonyloxy group", the "cycloalkylsulfonyl group" and the "cycloalkylsulfinyl group" includes the same as the cycloalkyl group as mentioned above.

The "cycloalkylcarbonyl group" includes a 3- to 8-membered monocyclic cycloalkylcarbonyl group, preferably a 4- to 6-membered cycloalkylcarbonyl group.

The "cycloalkylcarbonyloxy group" includes a 3- to 8-membered monocyclic cycloalkylcarbonyloxy group, preferably a 4- to 6-membered cycloalkylcarbonyloxy group.

The "cycloalkylsulfonyl group" includes a 3- to 8-membered monocyclic cycloalkylsulfonyl group, preferably a 4- to 6-membered cycloalkylsulfonyl group.

The "cycloalkylsulfinyl group" includes a 3- to 8-membered monocyclic cycloalkylsulfinyl group, preferably a 4- to 6-membered cycloalkylsulfinyl group.

The "cycloalkoxy" in the "cycloalkoxycarbonyl group" includes the same as the cycloalkoxy group as mentioned above. The "cycloalkoxycarbonyl group" includes a 3- to 8-membered monocyclic cycloalkoxylcarbonyl group, preferably a 4- to 6-membered cycloalkoxylcarbonyl group.

The "aryl" in the "aryloxy group", the "arylcarbonyl group", the "aryloxycarbonyl group", the "arylcarbonyloxy group", the "arylsulfonyl group" and the "arylsulfinyl group" includes the same as the aryl group as mentioned above. Examples of the "aryloxy group" are phenoxy, 1-naphthoxy or 2-naphthoxy. Examples of the "arylcarbonyl group" are benzoyl, 1-naphthaloyl or 2-naphthaloyl. Particularly, the "aryloxy-carbonyl group" includes phenoxycarbonyl, 1-naphthoxycarbonyl or 2-naphthoxycarbonyl. Examples of the "arylcarbonyloxy group" are benzoyloxy, 1-naphthoyloxy or 2-naphthoyloxy. Examples of the "aryl-sulfonyl group" are phenylsulfonyl, 1-naphthylsulfonyl, 2-naphthylsulfonyl. Examples of the "arylsulfinyl group" are phenylsulfinyl, 1-naphthylsulfinyl, 2-naphthylsulfinyl.

The "heteroaryl" in the "heteroaryloxy group", the "heteroaryl-carbonyl group", the "heteroaryloxycarbonyl group", the "heteroaryl-carbonyloxy group", the "heteroarylsulfonyl group" and the "heteroaryl-sulfinyl group" includes the same as the heteroaryl group as mentioned above. Examples of the "heteroaryloxy group" are pyrrolyloxy, pyridyloxy, pyrazinyloxy, pyrimidinyloxy, pyridazinyloxy, furyloxy, or thienyloxy. Examples of the "heteroarylcarbonyl group" are pyrrolyl-carbonyl, pyridylcarbonyl, pyrazinylcarbonyl, pyrimidinylcarbonyl, pyridazinylcarbonyl, furylcarbonyl, or thienylcarbonyl. Examples of the "heteroaryloxycarbonyl group" are pyrrolyloxycarbonyl, pyridyloxycarbonyl, pyrazinyloxycarbonyl, pyrimidinyloxycarbonyl, pyridazinyloxy-carbonyl, furyloxycarbonyl, or thienyloxycarbonyl. Examples of the "heteroarylcarbonyloxy group" are pyrrolylcarbonyloxy, pyridylcarbonyl-oxy, pyrazinylcarbonyloxy, pyrimidinylcarbonyloxy, pyridazinylcarbonyl-oxy, furylcarbonyloxy, or thienylcarbonyloxy. Examples of the "heteroarylsulfonyl group" are pyrrolylsulfonyl, pyridyl-sulfonyl, pyrazinylsulfonyl, pyrimidinylsulfonyl, pyridazinylsulfonyl, furylsulfonyl, or thienylsulfonyl. Examples of the "heteroarylsulfinyl group" are pyrrolylsulfinyl, pyridylsulfinyl, pyrazinylsulfinyl, pyrimidinylsulfinyl, pyridazinylsulfinyl, furylsulfinyl, or thienylsulfinyl.

The "saturated nitrogen-containing heterocycle" for $A^1$ includes a 4- to 8-membered saturated nitrogen-containing heterocycle containing 1 to 4 heteroatom(s) selected from 1 to 3 nitrogen atom(s), 0 to 1 oxygen atom and 0 to 1 sulfur atom (at least one of the heteroatom(s) is a nitrogen atom), and said sulfur atom may optionally be substituted by 1 or 2 oxygen atom(s). Examples thereof are azetidine, pyrrolidine, piperidine, piperazine, morpholine, thiomorpholine, thiomorpholin-1-oxide, thiomorpholine-1,1-dioxide, or perhydroazepine. In the formula (1), since $A^1$ is a divalent group, two hydrogen atoms on the above rings can be a binding bond.

Further, the "unsaturated nitrogen-containing heterocycle" for $A^1$ includes a 5- to 7-membered unsaturated non-aromatic nitrogen-containing heterocycle having 1 or 2 double bond(s), and further containing 1 to 2 heteroatom(s) (at least one of the heteroatom(s) is a nitrogen atom) selected from 1 to 2 nitrogen atom(s), 0 to 1 oxygen atom, and 0 to 1 sulfur atom, and said sulfur atom may optionally be substituted by 1 or 2 oxygen atom(s). Examples thereof are a 5-membered non-aromatic unsaturated nitrogen-containing heterocycle having one double bond within the ring thereof, or a 6- or 7-membered non-aromatic unsaturated nitrogen-containing heterocycle having 1 or 2 double bond(s) within the ring thereof. In the formula (1), since $A^1$ is a divalent group, 2 hydrogen atoms on the above rings can be a binding bond.

The "saturated or unsaturated nitrogen-containing saturated heterocycle" for $A^1$ preferably includes a divalent group selected from the saturated nitrogen-containing heterocyclic groups of the following formulae (2) to (16):

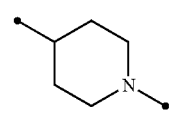

(2)

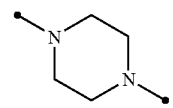

(3)

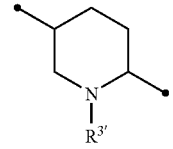

(4)

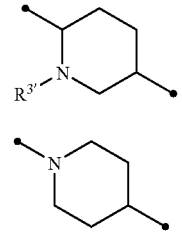

(5)

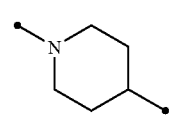

(6)

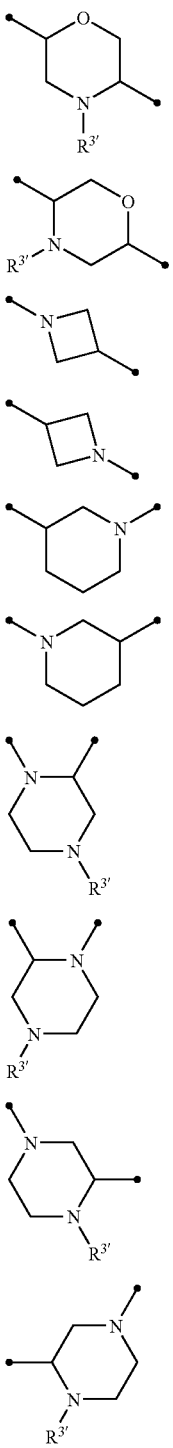

(wherein R³' is a hydrogen atom or a $C_{1-6}$ alkyl group), or a divalent group selected from the unsaturated non-aromatic heterocyclic groups, which are derived by replacing 1 or 2 of the ring-forming carbon-carbon bond(s) or carbon-nitrogen bond(s) of the above divalent groups by a double bond.

A¹ is more preferably selected from saturated nitrogen-containing divalent heterocycles of the above formulae (2) to (16). Especially preferable A¹ is a divalent group of the above formula (2), the formula (3) or the formula (6).

The aromatic carbocycle (aryl group) for A² is phenyl or naphthyl, and the binding position thereof is not necessarily specified.

The aromatic heterocycle (heteroaryl group) for A² includes a 5- to 10-membered monocyclic or bicyclic aromatic heterocycle (heteroaryl group) containing 1 to 4 heteroatom(s) selected from 0 to 3 nitrogen atom(s), 0 to 1 oxygen atom and 0 to 1 sulfur atom, and the binding position thereof is not necessarily specified, as long as it may be kept in chemically stable state. Examples thereof are furyl, thienyl, pyrrolyl, pyridyl, indolyl, isoindolyl, quinolyl, isoquinolyl, pyrazolyl, imidazolyl, pyrimidinyl, pyrazinyl, pyridazinyl, thiazolyl, or oxazolyl. Preferable one is a 5- or 6-membered aromatic heteromonocycle (heteroaryl group).

The substituted alkyl group, the substituted alkenyl group and the substituted alkynyl group are substituted by the same or different 1 or more substituents, preferably by 1 to 5 substituents, more preferably by 1 to 3 substituents.

The substituted cycloalkyl group and the substituted saturated heterocyclic group are substituted by the same or different 1 or more substituents, preferably by 1 to 5 substituents, more preferably by 1 to 3 substituents.

The substituted aryl group, the substituted heteroaryl group, the substituted aryloxy group and the substituted heteroaryloxy group are substituted by the same or different 1 or more substituents, preferably by 1 to 5 substituents, more preferably by 1 to 3 substituents.

The "nitrogen-containing saturated heterocycle" which is formed by combining two of the substituents of amino group, carbamoyl group or sulfamoyl group together with a nitrogen atom includes, for example, azetidine, pyrrolidine, piperidine, piperazine, morpholine, thiomorpholine, thiomorpholin-1-oxide, thiomorpholine-1,1-dioxide, perhydroazepine, etc.

In the formula (1), A² is preferably a substituted or unsubstituted phenyl group or a substituted or unsubstituted 5- or 6-membered aromatic heterocycle (heteroaryl group) containing at least one heteroatom selected from 0 to 2 nitrogen atom(s), 0 to 1 oxygen atom and 0 to 1 sulfur atom, and the substitution position thereof is not necessarily specified, as long as it may be kept in chemically stable state. More preferably A² is a substituted or unsubstituted phenyl, pyridyl or furyl group.

In the formula (1), suitable examples of the partial structure of "-L¹-A¹-L²-" are explained below.

When the nitrogen atom on the A¹ ring is attached to L¹, preferable L¹ is a group of the following (I) (where L¹ is attached to the adenine nucleus at the left side bond):

$$—(CH_2)_{2-8}— \qquad (I)$$

When the carbon atom on the A¹ ring is attached to L¹, preferable L¹ is a group of the following (II) or (III) (where L¹ is attached to the adenine nucleus at the left side bond):

$$—(CH_2)_{0-8}— \qquad (II)$$

$$—(CH_2)_{2-8}—NR^3— \text{ (R}^3 \text{ is the same as defined above)} \qquad (III)$$

When the nitrogen atom on the A¹ ring is attached to L², preferable L² is a carbonyl group, or a group of the following (IV) to (IX) (where L² is s attached to the adenine nucleus at the left side bond):

$$—(CH_2)_{0-5}— \qquad (IV)$$

$$—(CH_2)_{2-5}—O— \qquad (V)$$

$$—(CH_2)_{2-5}—NR^{3'}—(CH_2)_{0-3}— \qquad (VI)$$

$$-(CH_2)_{2-5}-NR^{3'}-(CH_2)_{2-3}-O- \quad (VII)$$

$$-(CH_2)_{0-5}-CO-(CH_2)_{0-2}-NR^{3'}-(CH_2)_{0-3}- \quad (VIII)$$

$$-(CH_2)_{0-5}-CO-(CH_2)_{0-2}-NR^{3'}-(CH_2)_{2-3}-O- \quad (IX).$$

When the carbon atom on the $A^1$ ring is attached to $L^2$, preferable $L^2$ is a carbonyl group, or a group of the following (X) to (XII) (where $L^2$ is attached to $A^1$ at the left side bond):

$$-(CH_2)_{0-5}-NR^{3'}-(CH_2)_{0-3}- \quad (X)$$

$$-(CH_2)_{0-5}-NR^{3'}-(CH_2)_{0-3}-O- \quad (XI)$$

$$-(CH_2)_{0-5}- \quad (XII)$$

$$-(CH_2)_{0-5}-O- \quad (XIII)$$

(in the above formula (VI) to (XI), $R^{3'}$ is a hydrogen atom or a $C_{1-6}$ alkyl group).

In the formula (1), $R^3$ is preferably a hydrogen atom or a $C_{1-3}$ alkyl group, more preferably a hydrogen atom or methyl.

In the formula (1), when X is $NR^2$, $R^2$ is preferably a hydrogen atom, or a $C_{1-3}$ alkyl group, more preferably a hydrogen atom or methyl. X is preferably an oxygen atom or a single bond.

In the formula (1), $R^1$ is preferably a substituted or unsubstituted $C_{1-6}$ straight chain or branched chain alkyl group. Examples thereof are a substituted or unsubstituted methyl, ethyl, propyl, butyl, pentyl, 1-methylethyl, 1-methylpropyl, or 2-methylbutyl group, and more preferably a $C_{1-4}$ straight chain alkyl group.

The substituent of the substituted alkyl group for $R^1$ is the same substituents for the alkyl group as mentioned above, and preferable substituents are a fluorine atom, a hydroxy group, a $C_{1-4}$ straight chain or branched chain alkoxy group, or a $C_{1-4}$ straight chain or branched chain alkylthio group, and said substituted alkyl group may have the same or different 1 or more substituents, preferably 1 to 5 substituents, more preferably 1 to 3 substituents. More preferable substituent is a hydroxy group or a $C_{1-3}$ straight chain or branched chain alkoxy group, and the number thereof is 1 to 3.

The adenine compounds of the present invention are intended to include all tautomers, geometric isomers or stereoisomers, and optionally, a mixture thereof, depending on the kinds of substituents.

In other words, in case that one or more asymmetric carbon atom(s) exist in the compound of the formula (1), diastereomers and enantiomers may also exist, and the present invention also includes mixtures of these diastereomers and enantiomers, and isolated forms thereof.

Additionally, the adenine compound of the formula (1) and a tautomer thereof are chemically equivalent, and the adenine compound of the present invention also includes the tautomer thereof. Particularly, the tautomer is in the form of hydroxy of the formula (1'):

(1')

(wherein $R^1$, $R^2$, $A^1$, $A^2$, X, $L^1$ and $L^2$ are as defined above)

A pharmaceutically acceptable salt includes acid addition salts and base addition salts. For example, the acid addition salt includes an inorganic acid salt such as hydrochloride, hydrobromide, sulfate, hydroiodide, nitrate, phosphate, etc., and an organic acid salt such as citrate, oxalate, acetate, formate, propionate, benzoate, trifluoroacetate, fumarate, maleate, succinate, tartrate, lactate, pyruvate, methane-sulfonate, benzenesulfonate, para-toluenesulfonate, etc. The base addition salt includes an inorganic base salt such as sodium salt, potassium salt, calcium salt, magnesium salt, ammonium salt, etc., and an organic base salt such as triethylammonium salt, triethanol ammonium salt, pyridinium salt, diisopropyl ammonium salt, etc., and additionally, amino acid salts such as basic or acidic amino acids including arginine, aspartic acid and glutamic acid, etc. The compound of the formula (1) may be a hydrate, or a solvate such as ethanolate.

The compound of the formula (1) may be prepared by the following methods. The starting compounds which are not described below may be prepared according to the following methods or known methods or those similar thereto.

Preparation Method 1

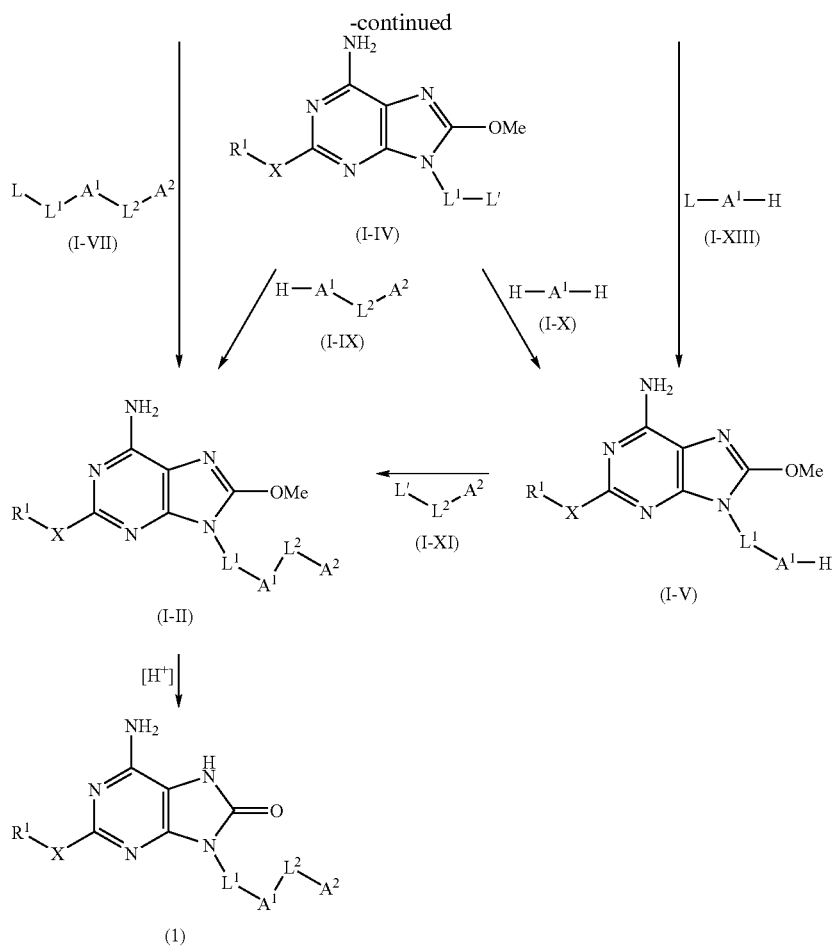

(wherein L and L' are a leaving group which may be the same or different, and A¹, A², R¹, X, L¹ and L² are the same as defined above)

The leaving group as defined herein means a halogen atom in the alkylation reaction or the acylation reaction, or a hydroxy group in the dehydration-condensation reaction, or an oxo group in the reductive alkylation reaction of amines, etc.

[Step 1]

The compound (I-II) is prepared by reacting the compound (I-I) with the compound (I-VII) in the presence of a base. For example, the compound (I-I) is condensed with a halide compound of the formula (I-VII) by the alkylation reaction. The base includes, for example, alkali metal carbonates such as sodium carbonate, potassium carbonate, etc., alkaline earth metal carbonates such as calcium carbonate, etc., metal hydroxides such as sodium hydroxide, potassium hydroxide, etc., metal hydrides such as sodium hydride, etc., metal alkoxides such as potassium t-butoxide, etc. The solvent includes, for example, aprotic solvents such as dimethylformamide, dimethyl sulfoxide, acetonitrile, etc., halogenated hydrocarbon solvents such as carbon tetrachloride, chloroform, methylene chloride, etc., ether solvents such as diethyl ether, tetrahydrofuran, 1,4-dioxane, etc. The reaction temperature is in the range of about 0° C. to around a boiling point of the solvent used.

[Step 2]

The compound of the formula (1) is obtained by treating the compound (I-II) under acidic conditions. The acid to be used in the acid-treatment includes, for example, inorganic acids such as hydrochloric acid, hydrobromic acid, sulfuric acid, etc., organic acids such as trifluoroacetic acid, etc. The solvent includes, for example, water, or a mixed solvent of water and an organic solvent. The above organic solvent includes, for example, ether solvents such as diethyl ether, tetrahydrofuran, etc., aprotic solvents such as dimethyl-formamide, acetonitrile, etc., alcohol solvents such as methanol, ethanol, etc. The reaction temperature is in the range of from room temperature to around a boiling point of the solvent used.

In addition, in the procedure of preparation of the compound (I-II) from the compound (I-I), the compound (I-II) can be obtained by reacting the compound (I-I) with the compound (I-VIII) in a similar manner to the above Step 1 to give the compound (I-IV), followed by reacting the compound (I-IV) with the compound (I-XI) by a well-known method to one of the ordinary skill in the art, such as by a similar method to the above Step 1, the dehydration-condensation reaction or the reductive alkylation reaction.

In the procedure of preparation of the compound (I-II) from the compound (I-IV), the compound (I-II) can also be obtained by reacting the compound (I-IV) with the compound (I-X) by a well-known method to one of the ordinary skill in the art, such as a similar method to the above Step 1, the dehydration-condensation reaction, or the reductive alkylation reaction to give the compound (I-V), followed by reacting the compound (I-V) with the compound (I-XI) in a similar manner to the above Step 1.

Further, in the procedure of preparation of the compound (I-V) from the compound (I-I), the compound (I-V) can also be obtained by reacting the compound (I-I) with the compound (I-XII) in a similar manner to the above Step 1 to give the compound (I-VI), followed by reacting the compound (I-VI) with the compound (I-XIII) by a well-known method to one of the ordinary skill in the art, such as a similar method to the above Step 1, the dehydration-condensation reaction or the reductive alkylation reaction.

[Step 3]

In addition, the compound (I-VII) and the compound (I-IX) may be prepared by the following methods.

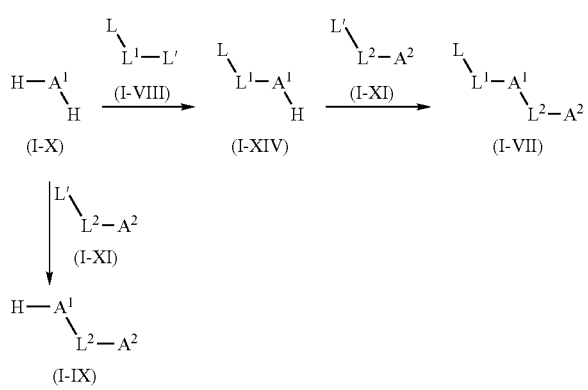

(wherein L, L', $A^1$, $A^2$, $L^1$ and $L^2$ are as defined above)

The compound (I-XIV) can be obtained by reacting the compound (I-X) with the compound (I-VIII) in the presence of a base. Subsequently, the compound (I-VII) can be obtained by reacting the compound (I-XIV) with the compound (I-XI) in the presence of a base.

In addition, the compound (I-IX) can be obtained by reacting the compound (I-X) with the compound (I-XI) in the presence of a base.

The base includes, for example, alkali metal carbonates such as sodium carbonate, potassium carbonate, etc., alkaline earth metal carbonates such as calcium carbonate, etc., metal hydroxides such as sodium hydroxide, potassium hydroxide, etc., organic bases such as triethylamine, diisopropylethylamine, pyridine, 4-dimethylamino-pyridine, etc., metal alkoxides such as sodium methoxide, etc. The solvent includes, for example, halogenated hydrocarbon solvents such as methylene chloride, etc., ether solvents such as diethyl ether, tetrahydrofuran, 1,4-dioxane, etc., alcohol solvents such as methanol, ethanol, etc., aprotic solvents such as dimethylformamide, dimethyl sulfoxide, acetonitrile, etc. The reaction temperature is in the range of from about 0° C. to around a boiling point of the solvent used.

In addition, when the compound of the present invention or an intermediate thereof has a functional group such as amino group, carboxyl group, hydroxy group, oxo group, etc., then the techniques of protection or de-protection may be employed. The preferable protecting group, a method of protection, and a method of de-protection are disclosed in detail in Protective Groups in Organic Synthesis 2nd Edition (John Wiley & Sons, Inc.; 1990), etc.

[Step 4]

Further, (I-1) may be prepared by the following method.

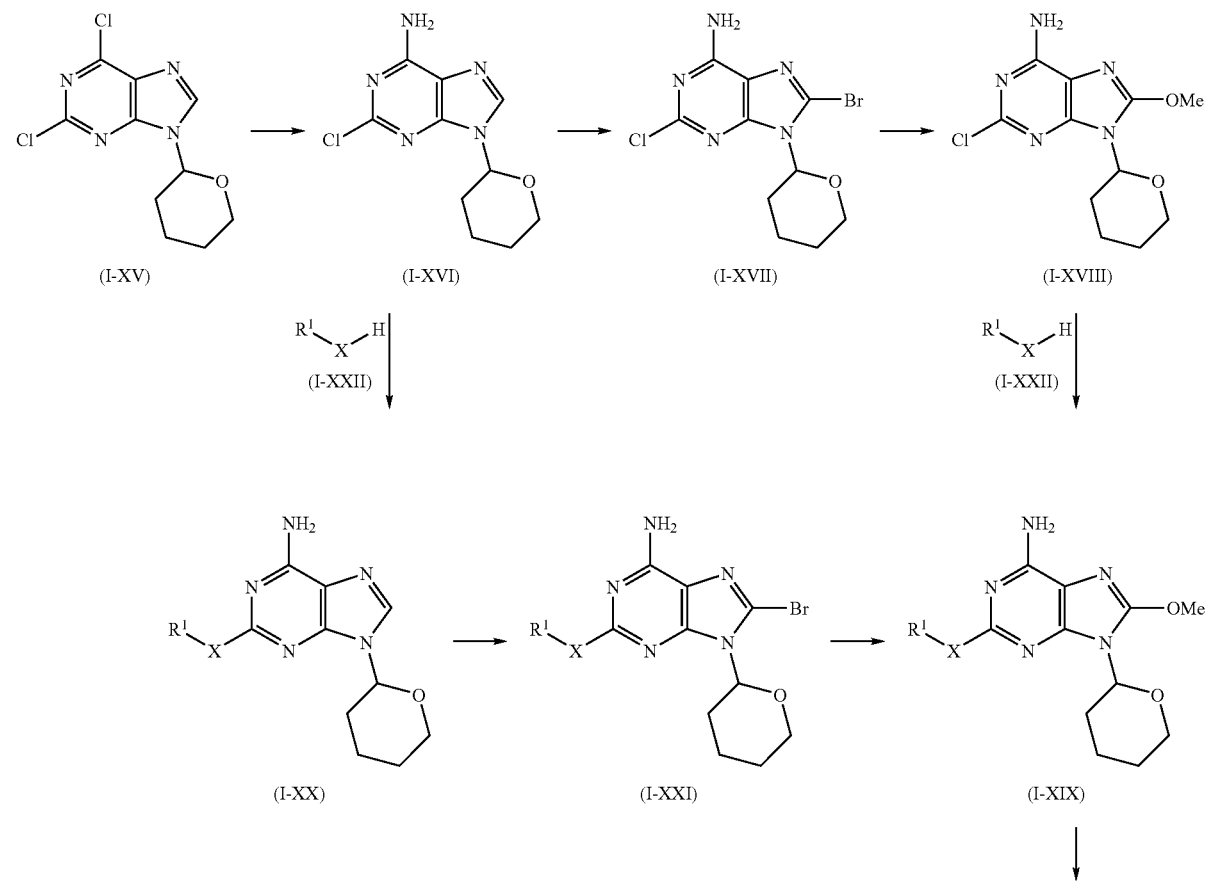

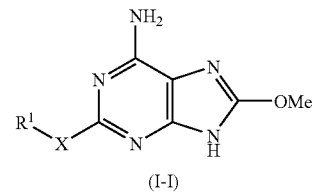

(I-I)

(wherein $R^1$ and X are as defined above)

The compound (I-XVI) may be obtained by reacting the compound (I-XV) with aqueous ammonia in water, or an organic solvent, or a mixed solvent of water and an organic solvent.

The organic solvent includes, for example, alcohol solvents such as methanol, ethanol, propanol, butanol, etc., ether solvents such as tetrahydrofuran, 1,4-dioxane, diglyme, etc., aprotic solvents such as acetonitrile, etc. The reaction temperature is, for example, in the range of from about room temperature to 200° C. This reaction may suitably be carried out in a reaction container such as autoclave.

The compound (I-XVII) may be prepared by bromination reaction of the compound (I-XVI). The brominating agent includes, for example, bromine, hydrobromide perbromide, N-bromosuccimide, etc. In the reaction, a reaction promoter such as sodium acetate may be added. The solvent includes, for example, halogenated hydrocarbon solvents such as carbon tetrachloride, methylene chloride, or dichloroethane, etc., ether solvents such as diethyl ether, etc., acetic acid, carbon disulfide, etc. The reaction temperature is, for example, in the range of from about 0° C. to around a boiling point of the solvent used.

The compound (I-XVIII) may be obtained by reacting the compound (I-XVII) with sodium methoxide.

The organic solvent includes, for example, ether solvents such as diethyl ether, tetrahydrofuran, 1,4-dioxane, etc., aprotic solvents such as dimethylformamide, etc., alcohol solvents such as methanol, etc. The reaction temperature is, for example, in the range of from room temperature to around a boiling point of the solvent used.

Further, the compound (I-XVIII) may also be obtained by treating the compound (I-XVII) with an aqueous alkaline solution containing methanol.

The aqueous alkaline solution includes, for example, an aqueous solution of alkali metal hydroxides such as sodium hydroxide, potassium hydroxide, etc. The reaction temperature is, for example, in the range of room temperature to around a boiling point of the solvent used.

The compound (I-XIX) may be obtained by reacting the compound (I-XVIII) with the compound (I-XXII).

When X is $NR^2$ ($R^2$ is as defined above), the reaction is carried out in the presence or absence of a base. The base includes, for example, alkali metal carbonates such as sodium carbonate, potassium carbonate, etc., alkaline earth metal carbonates such as calcium carbonate, etc., metal hydroxides such as sodium hydroxide, potassium hydroxide, etc., organic bases such as triethylamine, diisopropylethyl-amine, 4-dimethylaminopyridine, etc. The solvent includes, for example, ether solvents such as tetrahydrofuran, 1,4-dioxane, diglyme, etc., alcohol solvents such as propanol, butanol, etc., aprotic solvents such as dimethylformamide, etc., or the reaction may be carried out without a solvent. The reaction temperature is, for example, in the range of about 50° C. to 200° C.

When X is an oxygen atom or a sulfur atom, then the reaction is carried out in the presence of a base. The base includes, for example, alkali metals such as sodium, potassium, etc., alkali metal hydrides such as sodium hydride, etc. The solvent includes, for example, ether solvents such as tetrahydrofuran, 1,4-dioxane, diglyme, etc., aprotic solvents such as dimethylformamide, dimethyl sulfoxide, etc., or the reaction is carried out without a solvent. The reaction temperature is, for example, in the range of from about 50° C. to 200° C.

When X is $SO_2$, a synthetic intermediate where a corresponding X is a sulfur atom is oxidized with Oxone (registered trade name) or m-chloroperbenzoic acid (mCPBA).

In the process of preparing the compound (I-XIX) from the compound (I-XVI), the compound (I-XIX) may also be obtained by preparing the compound (I-XX) in a similar manner to the above, followed by converting the compound (I-XX) into the compound (I-XXI).

The compound (I-I) may be obtained by treating the compound (I-XIX) with trifluoroacetic acid in an organic solvent such as methanol.

The acid includes, for example, inorganic acids such as hydrochloric acid, hydrobromic acid, sulfuric acid, etc. or organic acids such as trifluoroacetic acid, etc. The solvent includes, for example, water, a mixed solvent of water and an organic solvent. The above-mentioned organic solvent includes ether solvents such as diethyl ether, tetrahydrofuran, etc., aprotic solvents such as dimethylformamide, acetonitrile, etc., alcohol solvents such as methanol, ethanol, etc. The reaction temperature is, for example, in the range of from room temperature to around a boiling point of the solvent used.

Preparation Method 2

When methylene for $L^2$ is replaced by $NR^3$ and $L^2$ is a group of the following formula (2) or the formula (3), then the desired compound may be prepared by the following method.

(wherein $Z^1$ and $Z^{2'}$ are an alkylene, $Z^2$ is a single bond or an alkylene, and $R^3$ is as defined above).

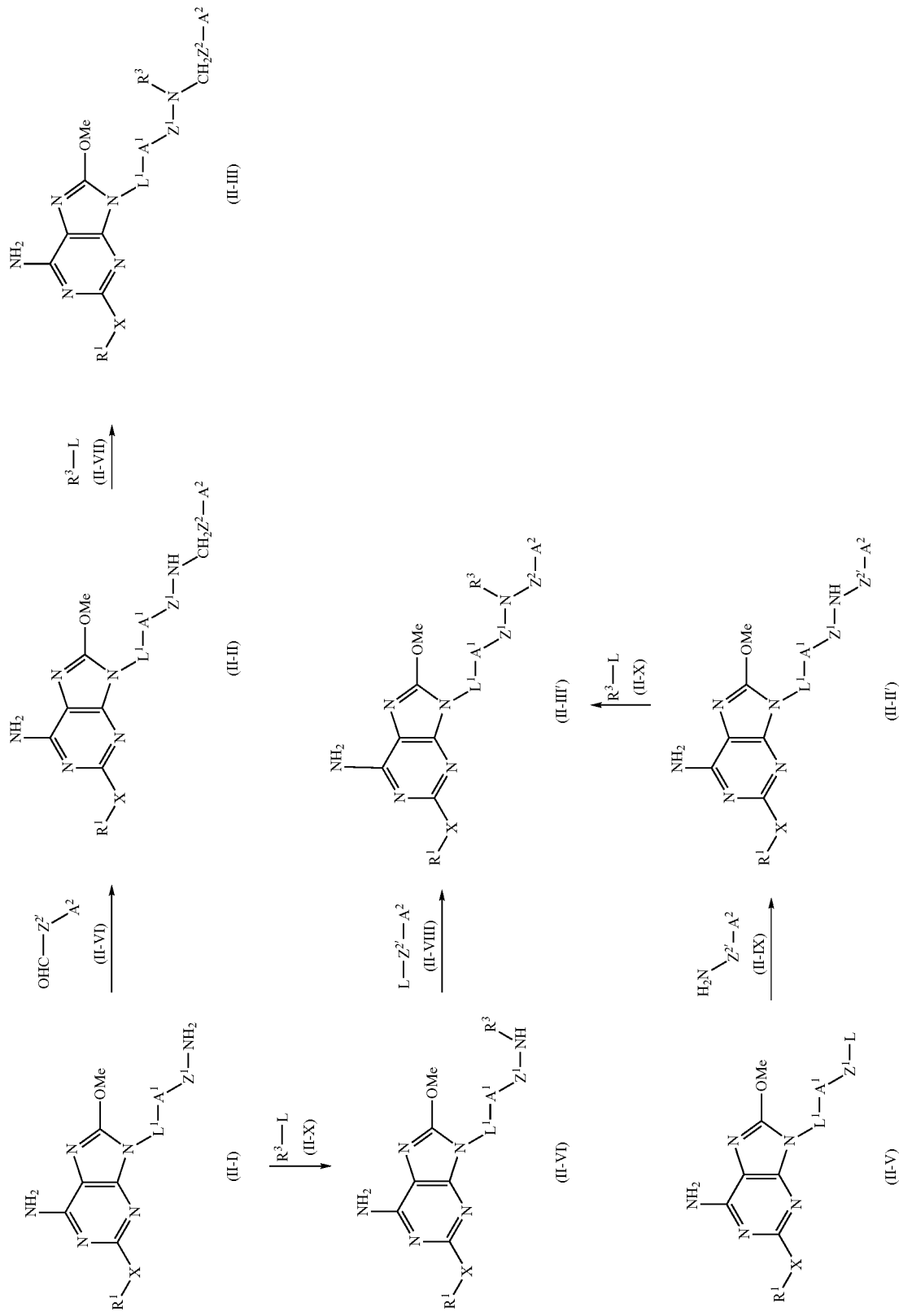

(wherein L, $L^1$, $A^1$, $A^2$, $R^1$, $R^2$, $R^3$, X, $Z^1$, $Z^2$ and $Z^{2'}$ are as defined above)

That is, the compound (II-II) may be obtained by reacting the compound (II-I) with an aldehyde compound of the formula (II-VI) in a solvent such as methanol, etc. by using a reducing agent such as sodium borohydride ($NaBH_4$), etc.

In addition, the compound (II-II') may be obtained by subjecting the compound (II-V) to the N-alkylation reaction with the compound (II-IX) in the presence or absence of a base. The based used in the N-alkylation reaction includes, for example, alkali metal carbonates such as sodium carbonate, potassium carbonate, etc., alkaline earth metal carbonates such as calcium carbonate, etc., metal hydroxides such as sodium hydroxide, potassium hydroxide, etc., organic bases such as triethylamine, diisopropylethylamine, 4-dimethylaminopyridine, etc. The solvent includes, for example, ether solvents such as tetrahydro-furan, 1,4-dioxane, diglyme, etc., alcohol solvents such as propanol, butanol, etc., aprotic solvents such as dimethylformamide, dimethyl-sulfoxide, acetonitrile, etc., or the reaction may be carried out without a solvent. The reaction temperature is, for example, in the range of room temperature to around a boiling point of the solvent used.

When $R^3$ is an alkyl group, the compound (II-III) may be obtained by reacting the compound (II-II) with an alkyl halide reagent of the formula (II-X) in a solvent such as acetonitrile, dimethylformamide, etc. in the presence of a base such as potassium carbonate, etc.

Alternatively, the compound (II-III') may be obtained by converting the compound (II-I) into the compound (II-VI) in a similar manner to the conversion reaction of the compound (II-II) into the compound (II-III) in Preparation Method 2, followed by subjecting the compound (II-VI) to the N-alkylation reaction as mentioned above.

The obtained compound (II-III) and the compound (II-III') may be converted into a 8-oxo compound, which the present compound, in a similar manner to the procedure of the preparation of the compound (1) from the compound (I-II) in Preparation Method 1.

Further, when the present compound, or an intermediate thereof has a functional group such as amino group, carboxyl group, hydroxy group, oxo group, etc., the techniques such as protection, de-protection, etc. may be employed. The preferable protecting groups, a method of protection, a method of de-protection are disclosed in detail in Protective Groups in Organic Synthesis 2nd Edition (John Wiley & Sons, Inc.; 1990), etc.

The compound of the formula (1) of the present invention or an intermediate for preparing said compound may be purified by a method known to those skilled in the art. For example, it may be purified by column chromatography (e.g., silica gel column chromatography, or ion-exchange column chromatography), or recrystallization, etc. The solvent which may be used in the recrystallization includes, for example, alcoholic solvents such as methanol, ethanol, 2-propanol, etc., ether solvents such as diethyl ether, etc., ester solvents such as ethyl acetate, etc., aromatic hydrocarbon solvents such as benzene, toluene, etc., ketone solvents such as acetone, etc., hydrocarbon solvents such as hexane, etc., aprotic solvents such as dimethylformamide, acetonitrile, etc., water, or a mixture thereof, etc. Other purification methods include a method described in Jikken-Kagaku-Koza (edited by the Chemical Society of Japan, Maruzen), vol. 1, etc.

The compound of the formula (1) with one or more asymmetric center(s) of the present invention may be prepared by using a starting material with asymmetric centers or introducing asymmetric centers in any half way steps according to a conventional method. For example, enantiomers may be obtained by using optically active starting materials or carrying out optical resolution in an appropriate step of the preparation. For example, the optical resolution may be carried out by a diastereomeric method wherein the compound of the formula (1) or an intermediate thereof is reacted with an optically active acid (e.g., mono-carboxylic acid such as mandelic acid, N-benzyloxyalanine, lactic acid, etc., dicarboxylic acid such as tartaric acid, o-diisopropylidene tartaric acid, malic acid, etc., or sulfonic acid such as camphorsulfonic acid, bromocamphorsulfonic acid, etc.) to form a salt thereof in an inert solvent (e.g., alcoholic solvent such as methanol, ethanol, 2-propanol, etc., ether solvent such as diethyl ether, etc., ester solvent such as ethyl acetate, etc., hydrocarbon solvent such as toluene, or aprotic solvent such as acetonitrile, etc., and a mixture thereof).

The optical resolution may be also carried out by reacting the compound of the formula (1) or an intermediate thereof having an acidic functional group such as carboxyl, etc. with an optically active amine (e.g., organic amine such as α-phenethylamine, quinine, quinidine, cinchonidine, cinchonine, strychnine) to form a salt thereof.

The temperature for forming the salt is selected from the range of from room temperature to a boiling point of the solvent used. In order to improve an optical purity, it is desirable to raise the temperature up to around a boiling point of the solvent. The precipitated salt may be cooled in the process of filtration in order to improve its yield, as necessary. The usage of an optically active acid or amine is properly in the range of about 0.5 to about 2.0 equivalents, preferably around 1 equivalent, to the substrate. The crystal may be also, as necessary, recrystallized in an inert solvent (e.g., alcoholic solvent such as methanol, ethanol, 2-propanol, etc., ether solvent such as diethyl ether, etc., ester solvent such as ethyl acetate, etc., hydrocarbon solvent such as toluene, etc., aprotic solvent such as acetonitrile, etc., and a mixture thereof) to give an optically active salt in high purity. The optically resolved salt may be also, as necessary, treated with an acid or a base in a conventional manner to give in a free form.

The adenine compound, or a pharmaceutically acceptable salt thereof of the present invention activates a Toll-like receptor (TLR), specifically TLR7, and is useful as an immune-regulating agent and a therapeutic or preventive agent for diseases such as diseases associated with abnormality of immune response (e.g., autoimmune diseases and allergic diseases), various infectious diseases wherein an immune response is desired to be activated, or cancers. For example, the adenine compound or a pharmaceutically acceptable salt thereof of the present invention is useful as a therapeutic or preventive agent for diseases including the following (1) to (8).

(1) Respiratory tract disease, including intermittent or persistent asthma of every severity (e.g., bronchial asthma, allergic asthma, intrinsic asthma, extrinsic asthma, exercise-induced asthma, asthma induced by drug (e.g., NSAID such as aspirin and indometacin), dust-induced asthma, and airway hyper-responsiveness caused by other factors); chronic obstructive lung disease (COPD); bronchitis (e.g., infectious bronchitis, eosinophilic bronchitis); emphysema; bronchiectasis; cystic fibrosis; sarcoidosis; farmer's lung and related diseases thereof; hypersensitivity pneumonitis; lung fibrosis (e.g., cryptogenic fibrosing alveolitis, idiopathic interstitial pneumonias, and fibrosis caused by antineoplastic therapy, chronic infectious diseases including *mycobacterium tuberculosis, aspergillus* or other fungal infectious diseases, etc.); complication by lung transplantation; vascular and thrombotic lung vasculature disease and pulmonary hypertension;

antitussive including treatment of chronic cough associated with inflammation or secretion of airway and iatrogenic cough; acute or chronic rhinitis including rhinitis medicamentosa or vasomotor rhinitis; perennial or seasonal allergic rhinitis including rhinitis nervosa (hay fever); nasal polyposis; acute virus infection including common cold disease and infectious diseases by respiratory syncytium virus, influenza, coronavirus (including SARS) and adenovirus;

(2) Skin diseases, including psoriasis, atopic dermatitis, contact dermatitis and other eczematous dermatoses, and delayed-type hypersensitivity reaction; phyto- and photodermatitis; seborrheic dermatitis, dermatitis herpetiformis; lichen planus, lichen sclerosis, lichen sclerosus et atrophicus, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilia, alopecia greata, male pattern baldness, Sweet's syndrome, Weber-Christian syndrome, erythema multiforme; infectious or noninfectious cellulitis; panniculitis; cutaneous lymphoma, nonmelanoma skin cancer or other dysplastic lesions; drug-induced disease including fixed drug eruption;

(3) Eye diseases, including blepharitis; conjunctivitis including perennial and vernal allergic conjunctivitis; iritis; anterior and posterior uveitis; choroiditis; retinal disease associated with autoimmune, degeneneration or inflammation; ophthalmitis including sympathetic ophthalmitis; sarcoidosis; viral, fungal or bacterial infectious diseases;

(4) Genitourinary diseases, including nephritis including interstitial and glomerulonephritis; nephrotic syndrome; cystitis including acute or chronic (interstitial) cystitis and Hunner's ulcer; acute or chronic urethritis, prostatitis, epididymitis, oophoritis and salpingitis; vulvovaginitis; Peyronie's disease; erectile dysfunction (male and female);

(5) Allograft rejections, including acute and chronic rejection after transplantation of kidney, heart, liver, lung, bone marrow, skin or cornea, or after blood transfusion, etc.; or chronic graft-versus-host disease;

(6) Autoimmune diseases, including chronic rheumatoid arthritis, inflammatory bowel diseases such as ulcerative colitis, systemic lupus erythematosus, multiple sclerosis, Hashimoto's thyroiditis, Grave's disease, Addison's disease, diabetes, idiopathic thrombocytopenic purpura, eosinophilic fasciitis, hyper IgE syndrome, antiphospholipid antibody syndrome or other autoimmune diseases and allergic diseases;

(7) Cancer diseases, including prostate cancer, breast cancer, lung cancer, uterus cancer, ovarian cancer, pancreatic cancer, liver cancer, colon cancer, stomach cancer, skin cancer or brain tumor, and malignant bone marrow neoplasm (e.g., leukemia) and lympho-proliferative tumor such as Hodgkin's lymphoma or non-Hodgkin's lymphoma. It is useful for usual treatment of these cancer diseases and also for prevention or treatment of metastasis, tumor recurrence and paraneoplastic syndrome;

(8) Infectious diseases, including viral infectious diseases such as infectious diseases caused by genital wart, common wart, plantar wart, hepatitis B, hepatitis C, herpes simplex viral disease, molluscum contagiosum, variola, acquired immune deficiency syndrome (HIV), or infectious diseases caused by human papillomavirus (HPV), cytomegalovirus (CMV), varicella-zoster virus (VZV), rhinovirus, adenovirus, coronavirus, influenza virus or parainfluenza virus; bacterial diseases such as tuberculosis, *mycobacterium avium*, or leprosy; other infectious diseases such as infectious diseases caused by various fungi, candida, chlamydia or *aspergillus*, cryptococcal meningitis, *pneumocystis carinii*, cryptosporidiosis, histoplasmosis, toxoplasmosis, trypanosome infectious diseases, or leishmaniasis.

The adenine compound or a pharmaceutically acceptable salt thereof of the present invention is also useful as a vaccine adjuvant.

The adenine compound or a pharmaceutically acceptable salt thereof of the present invention has a TLR activating effect, more specifically a TLR7 activating effect. The adenine compound or a pharmaceutically acceptable salt thereof of the present invention also shows interferon-α- and interferon-γ-inducing activity, and IL-4/IL-5 producing inhibitory activity, and acts as an agent with helper T cell type 1 (Th1 cell)/helper T cell type 2 (Th2 cell) selective immunoregulatory activity. In other words, it is preferably useful as a therapeutic or preventive agent for allergic diseases caused by Th2 cell such as asthma, COPD, allergic rhinitis, allergic conjunctivitis or atopic dermatitis due to its Th2 cell selective immunosuppressive action. On the other hand, owing to its immunostimulatory action, they are also useful as a therapeutic or preventive agent for various diseases, such as viral infectious diseases (e.g., cancer, hepatitis B, hepatitis C, acquired immune deficiency syndrome (HIV), human papillomavirus disease (HPV), etc.), bacterial infectious diseases, skin diseases (e.g., psoriasis), etc.

The adenine compound or a pharmaceutically acceptable salt thereof of the present invention is useful for treatment of airway obstruction diseases/conditions such as asthma or COPD, or for reducing the risk of these diseases.

The "preventive agent" of the present specification is intended to mean an agent to be administered to a patient who has not been affected with a disease or whose health condition is not so bad at the moment of administration, in order to avoid the onset of a disease or the aggravation of conditions. The "preventive" has been expected to be effectual especially for a person who had shown the symptoms of said disease before, or who is considered to have an increasing disease risk. A person who has a risk for onset of a specific disease or who has a risk for aggravation of diseased state can be identified, for example, by its family line being easily affected with said disease, or gene diagnosis, or diagnosis of said disease.

The adenine compound or a pharmaceutically acceptable salt thereof of the present invention may be orally or parenterally administered without any limitation to the dosage forms. For example, an oral preparation may include capsules, powders, tablets, granules, subtle granules, syrups, liquids, suspensions, etc., and a parenteral preparation may include injections, drips, eye-drops, preparations for intrarectal administration, inhalations, air sprays (e.g., liquid/-suspensions for sprays, aerosols, dry powders or for cartridge sprays for inhalators or insufflators, etc.), lotions, gels, ointments, creams, transdermal absorbents, transmucosal absorbents, nasal preparations, eardrops, tapes, transdermal patches, cataplasms, external powders, etc. These preparations may be formulated according to a conventional technique, and may contain conventional carriers, excipients, binders, lubricants, stabilizers, disintegrants, buffers, solubilizing agents, isotonic agents, surfactants, antiseptic agents, perfumes, etc., and further optionally contains two or more kinds of additives for preparations.

The adenine compound or a pharmaceutically acceptable salt thereof of the present invention may be incorporated with a pharmaceutically acceptable carrier in a manner known to those skilled in the art to prepare a pharmaceutical composition suitable for each dosage form. For example, the adenine compound or a pharmaceutically acceptable salt thereof may be formed into a pharmaceutical composition comprising as the active ingredient 0.05 to 99% by weight, preferably 0.05 to 80% by weight, more preferably 0.1 to 70% by weight, more preferably 0.1 to 50% by weight of the compound.

Among the oral preparations, liquid preparations such as emulsions and syrups may be prepared by optionally using additives for preparations including water; sugars such as sucrose, sorbit, fructose; ethanol; glycols such as polyethyleneglycol, propyleneglycol, glycerol; oils such as sesame oil, olive oil, soybean oil; preservative such as p-hydroxybenzoate; sweetener such as saccharin; thickener such as carboxymethylcellulose; flavors such as strawberry flavor, peppermint flavor, or colorants, etc.

Solid preparations such as capsules, tablets, powders, granules, etc. may be prepared by optionally compounding the following carriers. Specifically, they may be prepared by using excipients such as lactose, glucose, sucrose, sorbitol, mannitol (mannite), cellulose derivatives; disintegrants such as starch (e.g., potato starch, cornstarch, amylopectin), sodium alginate; lubricants such as magnesium stearate, calcium stearate, polyethyleneglycol, wax, paraffin, talc; binders such as polyvinyl alcohol, polyvinylpyrrolidone, hydroxypropylcellulose, gelatin; surfactants such as fatty acid ester; plasticizers such as glycerin, etc. Sugar coated tablets may be coated by concentrated carbohydrate solutions, optionally containing gum arabic, gelatin, talc, titanium oxide, etc., on the tablet cores prepared by using the above carriers. Alternatively, tablets may be film-coated with appropriate polymers dissolved in organic solvents which may be easily distilled away.

Soft gelatin capsules may be prepared by, for example, compounding the present compound with a vegetable oil or polyethyleneglycol. Hard gelatin capsules may be prepared by using granules of the present compound which may be prepared by optionally compounding any one of the above carriers.

Among the parenteral preparations, liquid preparations in the form of injections, drips, eye-drops, eardrops, etc. may be preferably prepared as sterile isotonic liquid preparations. For example, the injections may be prepared by using aqueous media comprising saline solution, glucose solution, or a mixture of saline solution and glucose solution. The preparations for intrarectal administration may be prepared by using carriers such as cacao butter, and usually prepared in the form of suppositories.

The ointments, creams and gels usually contain 0.01 to 10 w/w % of the present compound, and a preferable thickener and/or a gelatinizing agent and/or a solvent may be optionally added to aqueous or oily base. For example, the base includes water and/or oil such as liquid paraffin, vegetable oil such as peanut oil or castor oil, or solvent such as polyethyleneglycol. The thickener and the gelatinizing agent include soft paraffin, aluminum stearate, cetostearyl alcohol, polyethyleneglycol, lanolin, bee wax, carboxypolymethylene and cellulose derivative and/or glyceryl monostearate and/or nonionic emulsifier.

The lotions usually contain 0.01 to 10 w/w % of the present compound, and may be formulated by aqueous or oily base, and may typically comprise an emulsifier, a stabilizer, a dispersing agent, a precipitation inhibitor or a thickener.

The external powders usually contain 0.01 to 10 w/w % of the present compound, and may be formulated with preferable powder base such as talc, lactose or starch.

The drips may be formulated by aqueous or nonaqueous base and may contain a dispersing agent, a solubilizer, a precipitation inhibitor or a preservative.

The air spray (e.g., spray, aerosol, dry powder preparation, etc.) may be optionally formulated as aqueous solution or suspension, or aerosol delivered from pressurized pack such as quantitative dose inhalator by using, for example, a preferable liquefied propellant. Dry powder preparation may be also used.

The aerosol appropriate for inhalation may be either suspension or solution, and typically contains the present compound and any appropriate propellants such as fluorocarbon or hydrogen-containing chlorofluorocarbon or a mixture thereof. Specifically, it contains hydrofluroalkane, particularly 1,1,1,2-tetrafluoroethane, heptafluoro-alkane (HFA) such as 1,1,1,2,3,3,3-heptafluoro-n-propane, or a mixture thereof. The aerosol may optionally contain additional preparation excipient well-known to those skilled in the art such as surfactants (e.g., oleic acid or lecithin) and cosolvents (e.g., ethanol), etc. Specifically, it may include an inhalator known as "Turbuhaler (registered trande name)".

For example, capsule or cartridge of gelatin used in an inhalator or an insufflator may be formulated containing a powder mixture for inhalation of the compound used in the present invention and a preferable powder base such as lactose or starch. Each capsule or cartridge usually contains 20 μg to 10 mg of the present compound. Alternatively, the compound used in the present invention may be provided without an excipient such as lactose.

In case of oral or nasal inhalation as pressurized HFA aerosol and dry powder preparation, etc., the adenine compound or a pharmaceutically acceptable salt thereof of the present invention may be finely ground into 10 μm or less and they are suspended in a fatty acid with 8 to 20 carbon atoms or a salt thereof (e.g., oleic acid), bile acid salt, phospholipid, alkyl saccharide, fully-fluorinated or polyethoxylated surfactant, or other pharmaceutically acceptable dispersing agent.

It is preferable that the adenine compound of the present invention is parenterally administered as a preparation for local administration. Specifically, the preferable preparation includes ointments, lotions (solutions or suspensions), creams, gels, tapes, transdermal patches, cataplasms, sprays, aerosols, dry powder preparations, water/suspensions for cartridge sprays for inhalator or insufflator, eye-drops, eardrops, nasal drops, transdermal patches, lung absorbents, airway absorbents or external powders, etc.

In the preparation for local administration in the present invention, the ratio of the active compound used in the present invention is generally in the range of 0.001 to 10% by weight, preferably in the range of 0.005 to 1% by weight, depending on the forms of preparations. The ratio used in powders for inhalation or ventilation is in the range of 0.1 to 5% by weight.

Each quantitative dose or "one-sprayed amount" in the aerosols preferably contains 20 μg to 2000 μg, preferably about 20 μg to 500 μg of the compound used in the present invention. The administration may be once or several times a day, for example, 2, 3, 4 or 8 times a day, and 1, 2 or 3 dosage unit(s) are administered in each administration.

The pharmacological activity may be measured in any assessments well-known to those skilled in the art, preferably in vitro assessments. Specific measuring method includes the one described in Example in the present specification.

The present invention also encompasses a combination therapy for treating diseases described in the present specification wherein the compound of the formula (1) or a pharmaceutically acceptable salt thereof, or a pharmaceutical composition comprising the compound of the formula (1) or a pharmaceutically acceptable salt thereof is sequentially or simultaneously administered in combination with 1 or more of the following other medicaments.

Particularly, the medicaments for treating inflammatory diseases, COPD, asthma and allergic rhinitis include TNF-α inhibitors such as anti TNF monoclonal antibody (e.g., infliximab (REMICADE), CDP-870 and adalimumab) or TNF receptor immunoglobulin molecule (e.g., etanercept (ENBREL)); locally- or systemically-administered nonselective cyclooxygenase: COX-1/COX-2 inhibitor (e.g., piroxicam, diclofenac, propionic acids such as naproxen, flurbiprofen, fenoprofen, ketoprofen and ibuprofen, fenamate such as mefenamic acid, indomethacin, sulindac, azapropazone, pyrazolone such as phenylbutazone, salicylate such as aspirin), COX-2 inhibitor (e.g., meloxicam, celecoxib, rofecoxib, valdecoxib, lumarocoxib, parecoxib and etoricoxib); glucocorticoid which is administered locally, orally, intramuscularly, intravenously or intraarticularly; methotrexate, leflunomide; hydroxychloroquine, d-penicillamine, auranofin, or other parenteral or oral gold preparation, etc.

The present invention also encompasses a combination of the present compound with leukotriene biosynthetic inhibitor, 5-lipoxygenase (5-LO) inhibitor or 5-lipoxygenase activated protein (FLAP) antagonist, for example, zileuton; ABT-761; fenleutone; tepoxalin; ABBOTT-79175; ABBOTT-85761; N-(5-substituted)-thiophen-2-alkyl-sulfonamide; 2,6-di-tert-butylphenolhydrazone; methoxytetrahydropyrane such as ZENECA ZD-2138; SB-210661; pyridinyl-substituted-2-cyanonaphthalene compound such as L-739010; 2-cyanoquinoline compound such as L-746530; MK-591, MK-886 and BAY-X-1005, etc.

The present invention also encompasses a combination therapy of the present compound with leukotriene (LT) B4, LTC4, LTD4, LTE4 receptor antagonist selected from the following group: phenothiazine compound such as L-651392; amidino compound such as CGS-25019c; benzoxalamine such as ontazolast; benzenecarboxylmidamide such as BIIL284/260; and compounds such as zafirlukast, ablukast, montelukast, pranlukast, verlukast (MK-679), RG-12525, Ro-245913, iralukast (CGP45715A) and BAY-X-7195, etc.

The present invention also encompasses a combination therapy of the present compound with phosphodiesterase (PDE) inhibitor such as methylxanthanin including theophylline and aminophylline; selective PDE isoenzyme including PDE4 inhibitor, isoform PDE4D inhibitor or PDE5 inhibitor.

The present invention also encompasses a combination therapy of the present compound which is orally or topically administered with, for example, histamine H1 receptor antagonist such as cetirizine, loratadine, desloratadine, fexofenadine, acrivastine, terfenadine, astemizole, azelastine, levocabastine, chlorpheniramine, promethazine, cyclizine, mizolastine, etc.

The present invention also encompasses a combination therapy of the present compound with histamine type 4 receptor antagonists.

The present invention also encompasses a combination therapy of the present compound with α1/α2 adrenaline receptor agonist and vasoconstrictive sympathetic stimulant such as propylhexedrine, phenylephrine, phenylpropanolamine, ephedrine, pseudoephedrine, naphazoline hydrochloride, oxymetazoline hydrochloride, tetra-hydrozoline hydrochloride, xylometazoline hydrochloride, tramazoline hydrochloride, or ethyl norepinephrine hydrochloride.

The present invention also encompasses a combination therapy of the present compound with anticholinergic agent including muscarinic receptor (M1, M2 and M3) antagonist such as atropine, hyoscine, glycopyrrolate, ipratropium bromide; tiotropium bromide; oxytropium bromide; pirenzepine; or telenzepine.

The present invention also encompasses a combination therapy of the present compound with β-adrenaline receptor agonist including β receptor subtypes 1 to 4 such as isoprenaline, salbutamol, formoterol, salmeterol, terbutaline, orciprenaline, bitolterol mesylate or pirbuterol.

The present invention also encompasses a combination therapy of the present compound with chromone such as sodium cromoglycate or nedocromil sodium.

The present invention also encompasses a combination therapy of the present compound with insulin-like growth factor type 1 (IGF-1) mimic.

The present invention also encompasses a combination therapy of the present compound with inhaled glucocorticoid such as flunisolide, triamcinolone acetonide, beclomethasone dipropionate, budesonide, fluticasone propionate, ciclesonide or mometasone furoate.

The present invention also encompasses a combination therapy of the present compound with matrix metalloprotease inhibitor, specifically inhibitor of stromelysin, collagenase, gelatinase, aggrecanase, particularly collagenase-1 (MMP-1), collagenase-2 (MMP-8), collagenase-3 (MMP-13), stromelysin-1 (MMP-3), stromelysin-2 (MMP-10) and stromelysin-3 (MMP-11), MMP-9 or MMP-12.

The present invention also encompasses a combination therapy of the present compound with chemokine receptor regulators of antagonists of CCR1, CCR2, CCR2A, CCR2B, CCR3, CCR4, CCR5, CCR6, CCR7, CCR8, CCR9, CCR10 and CCR11 (CC family); CXCR1, CXCR2, CXCR3, CXCR4 and CXCR5 (C—X—C family); C—X3-C family such as CX3CR1.

The present invention also encompasses a combination therapy of the present compound with cytokine function regulator including cytokine or medicaments acting on cytokine signaling pathway, for example, α-, β- and γ-interferon, interleukin (IL) including IL1 to 15, and interleukin antagonist or inhibitor.

The present invention also encompasses a combination therapy of the present compound with immunoglobulin (Ig), immunoglobulin preparations, or antibodies and antagonists regulating Ig functions such as anti IgE antibody (omalizumab).

The present invention also encompasses a combination therapy of the present compound with systemically- or locally-administered anti-inflammatory drugs such as thalidomide or derivatives thereof, retinoid, dithranol or calcipotriol.

The present invention also encompasses a combination therapy of the present compound with antibacterial agents such as penicillin derivative, tetracycline, macrolide, β-lactam, fluoroquinolone, metronidazole and inhaled aminoglycoside; and antiviral agents including acyclovir, famciclovir, valaciclovir, ganciclovir, cidofovir, amantadine, rimantadine, ribavirin; zanamivir, oseltamavir; enzyme inhibitor such as indinavir, nelfinavir, ritonavir and saquinavir; nucleoside reverse transcriptase inhibitor such as didanosine, lamivudine, stavudine, zalcitabine, zidovudine; or nonnucleoside reverse transcriptase inhibitor such as nevirapine or efavirenz.

The present invention also encompasses a combination therapy of the present compound with medicaments known as therapeutic agents for cancer. Preferable agents include the following medicaments.

(i) Antiproliferative agents/antitumor agents and a combination thereof used as a therapeutic agent for tumors, for example, alkylating agents (e.g., cisplatin, carboplatin, oxaliplatin, miriplatin, cyclophosphamide, nitrogen mustard, melphalan, chlorambucil, busulfan, temozolamide, or nitrosourea); antimetabolite (e.g., fluoropyrimidine such as 5-fluorouracil and tegafur, antifolate such as raltitrexed, methotrexate, cytosine arabinoside, hydroxyurea, gemcitabine or paclitaxel); antineoplastic antibiotics (e.g., anthracycline such as adriamycin, bleomycin, doxorubicin, amrubicin, daunomycin, epirubicin, idarubicin, mitomycin-C, dactinomycin, or mithramycin); antimitotic agents (e.g., vinca alkaloid such as vincristine, vinblastine, vindesine or vinorelbine, taxoid such as taxol or taxotere); or topoisomerase inhibitors (e.g., epipodophyllotoxins such as etoposide, teniposide, amsacrine, topotecan or camptothecin).

(ii) Cytostatic agents including antiestrogens (e.g., tamoxifen, toremifene, raloxifene, droloxifene or iodoxifene, etc.), estrogen receptor down regulators (e.g., fulvestrant), antiandrogenic agents (e.g., bicalutamide, flutamide, nilutamide, or cyproterone acetate), LHRH antagonists or LHRH agonists (e.g., goserelin, leuprorelin or buserelin), progestogen (e.g., megestrol acetate), aromatase inhibitors (e.g., anastrozole, letrozole, vorazole or exemestane) and 5α-reductase inhibitors (e.g., finasteride).

(iii) Inhibiting agents of invasion of cancer cells (e.g., c-Src kinases family inhibitors such as 4-(6-chloro-2,3-methylenedioxyanilino)-7-[2-(4-methylpiperazin-1-yl)ethoxy]-5-tetrahydropyran-4-yloxyquinazoline (AZD0530; International Patent Publication WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661), etc., metalloprotease inhibitors such as marimastat, etc., or inhibitors of urokinase plasminogen activating receptor functions, or heparanase antibody).

(iv) Growth factor function inhibitors: for example, growth factor antibody, and growth factor receptor antibody (e.g., anti-erbb2 antibody trastuzumab (Herceptin (registered trade name)), anti-erbB1 antibody cetuximab [Erbitux, C225], and growth factor or growth factor receptor antibody disclosed in Stern et al., Critical reviews in oncology/-haematology, 2005, 54, 11-29); tyrosine kinase inhibitors such as epidermal growth factor inhibitors such as EGFR family tyrosine kinase inhibitors (e.g., N-(3-chloro-4-fluorophenyl)-7-methoxy-6-(3-morpholino-propoxy)quinazolin-4-amine (Gefitinib, AZD1839), N-(3-ethynylphenyl)-6,7-bis(2-methoxyethoxy)quinazolin-4-amine (erlotinib, OSI-774) and 6-acrylamide-N-(3-chloro-4-fluorophenyl)-7-(3-morpholinopropoxy)-quinazolin-4-amine (CI1033)); erbB2 tyrosine kinase inhibitors such as lapatinib, hepatocellular growth factor family inhibitors, platelet-derived growth factor family inhibitors such as imatinib, serine/threonine kinase function inhibitors (e.g., Ras/Raf signaling inhibitors such as farnesyl transferase inhibitors including sorafenib (BAY 43-9003)), MEK and/or AKI kinase cell signaling inhibitors, c-kit inhibitors, abl kinase inhibitors, IGF (insulin-like growth factor) receptor kinase inhibitors; and aurora kinase inhibitors (e.g., AZD1152, PH739358, VX-680, MLN8054, R763, MP235, MP529, VX-528 and AX39459) and CDK2 and/or CDK4 inhibitor cyclin-dependent kinase inhibitors.

(v) Antiangiogenic agents, for example, inhibiting agents of activity of vascular endothelial cell growth factor (e.g., anti-vascular endothelial cell growth factor antibody bevacizumab (Avastin (registered trade name)), and VEGF receptor kinase inhibitors such as 4-(4-bromo-2-fluoroanilino-6-methoxy-7-(1-methylpiperidin-4-ylmethoxy)quinazoline (ZD6474; Example 2 of WO 01/32651), 4-(4-fluoro-2-methylindol-5-yleoxy)-6-methoxy-7-(3-pyrrolidin-1-ylpropoxy)quinazoline (AZD2171; Example 240 of WO 00/47212), vatalanib (PTK787; WO 98/35985) and SU11248 (sunitinib; WO 01/60814), compounds disclosed in international publications: WO97/22596, WO97/30035, WO97/32856 or WO98/13354, and compounds acting in other mechanisms (e.g., linomid, integrin αvβ3 function inhibitors or angiostatin).

(vi) Vascular damaging agents such as combretastatin A4 or compounds disclosed in international publications: WO 99/02166, WO 00/40529, WO 00/41669, WO 01/92224, WO 02/04434 and WO 02/08213.

(vii) Antisense therapeutics, for example, antisense to the above targets such as ISIS2503, anti-ras antisense.

(viii) Gene therapy, for example, aberrant gene exchanging approach such as aberrant p53 and aberrant BRCA1 or BRCA2, GDEPT (Gene-directed enzyme pro-drug therapy) approach using cytosine deaminase, thymidine kinase or bacterial nitroreductase enzyme, approach enhancing patients' tolerance for chemotherapy or radiotherapy such as multi drug resistance gene therapy.

(ix) Immunotherapy approach, for example approach for enhancing immunity to cancer cells of patients by exposuring cytokine such as interleukin 2, interleukin 4 or Granulocyte-Macrophage Colony Stimulating Factor (GM-CSF) ex-vivo or in-vivo, T cell energy reducing approach, approach transplanting immune cells such as cytokine exposed dendritic cells, approach using cytokine exposed tumor cell line, and approach using anti-idiotypic antibody, etc.

EXAMPLES

The following compounds were prepared according to the Preparation Methods described in the present specification. The abbreviations in the present specification are as follows.
EtOAc: ethyl acetate
DCM: dichloromethane
NBS: N-bromosuccinimide
DMF: N,N-dimethylformamide
DMSO: dimethyl sulfoxide
THF: tetrahydrofuran
TFA: trifluoroacetic acid
MS: mass spectrometry
APCI: Atmospheric Chemical Ionization Method
HCl: hydrochloric acid In the reverse-phase HPLC, "Waters SYMMETRY C8, XTERRA OR PHENOMENEX GEMINI columns" was used herein, and acetonitrile and buffer (e.g., aqueous ammonium acetate solution, aqueous ammonia solution, aqueous formic acid solution or aqueous trifluoroacetic acid solution) were used as an elution solvent. Column chromatography was carried out using silica gel. In addition, SCX means solid phase extraction using sulfonic acid adsorbent, where a mixture is adsorbed onto the sulfonic acid adsorbent and eluted with a solvent such as methanol, acetonitrile, etc. Subsequently, a released basic product is eluted with a solvent such as aqueous ammonia/methanol acetonitrile, etc.

The present invention will be illustrated in more detail by the following Examples, but it should not be construed to be limited thereto.

Example 1

Synthesis of 2-butoxy-7,8-dihydro-9-(3-[4-(4-methylbenzyl)piperazin-1-yl]propyl)-8-oxoadenine

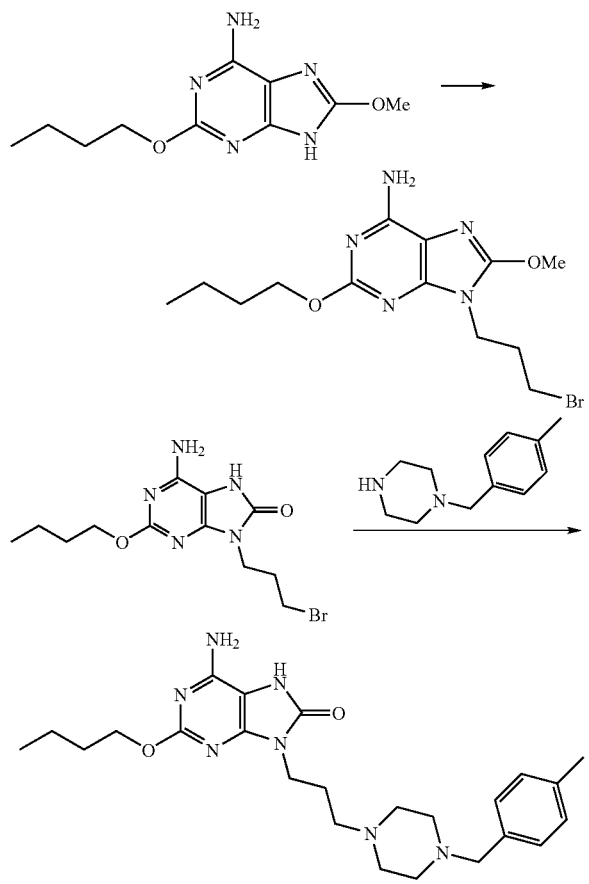

Step (i)

9-(3-Bromopropyl)-2-butoxy-8-methoxy-9H-purin-6-ylamine

To a solution of 2-butoxy-8-methoxyadenine (5 g, 14.2 mmol) in dimethylformamide (50 ml) were added 1,3-dibromobutane (7.2 ml) and potassium carbonate (9.2 g), and the mixture was stirred at room temperature for 1.5 hour. Water (200 ml) and ethyl acetate (75 ml) were added thereto, and the mixture was extracted, and further extracted with ethyl acetate (75 ml) twice. The organic layers were combined, dried over magnesium sulfate, filtered, and the solvent was distilled off under reduced pressure. To the residue was added diethyl ether (25 ml), and the precipitated crystals were collected by filtration, washed with ether (5 ml), and dried to give the subtitle compound (3.6 g) as a white solid. Yield: 71%

$^1$H NMR (CDCl$_3$) δ 5.24 (2H, brs), 4.29 (2H, t, J=6.7 Hz), 4.13 (3H, s), 4.09 (2H, t, J=6.7 Hz), 3.38 (2H, t, J=6.6 Hz), 2.34 (2H, q, J=6.6 Hz), 1.80-1.73 (2H, m), 1.54-1.46 (2H, m), 0.96 (3H, t, J=7.4 Hz).

Step (ii)

2-Butoxy-9-(3-bromopropyl)-7,8-dihydro-8-oxoadenine

To a solution of the compound (1 g, 2.79 mmol) obtained in Step (i) in methanol (2 ml) was added a 4N-hydrochloric acid in dioxane (2 ml), and the mixture was stirred at room temperature for 3.5 hours. The mixture was neutralized by addition of 28% aqueous ammonia at 0° C., and the mixture was stirred for one hour. The precipitated crystals were collected by filtration, washed twice with water (2 ml) and further washed twice with methanol (2 ml), and dried to give the subtitle compound (882 mg) as a white solid. Yield: 92%

$^1$H NMR (CDCl$_3$) δ 9.89 (1H, brs), 6.43 (2H, s), 4.16 (2H, t, J=6.6 Hz), 3.80 (2H, t, J=6.6 Hz), 3.53 (2H, t, J=6.6 Hz), 2.20 (2H, q, J=6.6 Hz), 1.68-1.61 (2H, m), 1.42-1.36 (2H, m), 0.92 (3H, t, J=7.4 Hz).

Step (iii)

The compound (180 mg) obtained in Step (ii), potassium carbonate (140 mg) and 4-methylbenzylpiperazine (130 mg) were added to DMF (5 mL), and the mixture was stirred at 70° C. for 3 hours. The insoluble materials were collected by filtration, and the residue was purified by silica gel column chromatography (CHCl$_3$:MeOH:28% NH$_3$ aq.=100:3:2) to give the title compound (48 mg).

$^1$H NMR (DMSO-d$_6$) δ 9.82 (1H, s), 7.15 (2H, d, J=8.0 Hz), 7.11 (2H, d, J=8.0 Hz), 6.39 (2H, s), 4.13 (2H, t, J=6.6 Hz), 3.69 (2H, t, J=6.8 Hz), 3.36 (2H, s), 3.64 (2H, s), 3.61 (3H, s), 2.27 (12H, m), 1.76 (2H, m), 1.62 (2H, m), 1.36 (2H, m), 0.90 (3H, t, J=7.2 Hz).

By the same method as Example 1, the compounds of the following Examples 2 to 8 were synthesized.

Example 2

9-(3-[4-Benzylpiperidin-1-yl]propyl)-2-butoxy-7,8-dihydro-8-oxoadenine

Yield: 41%

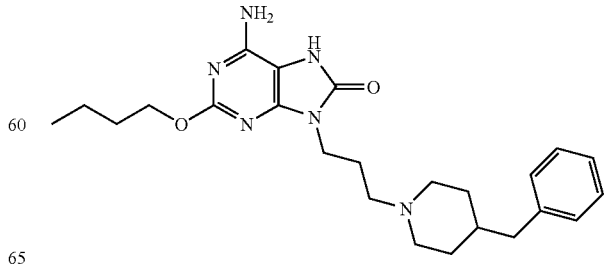

¹H NMR (DMSO-d₆) δ 9.80 (1H, s), 7.26 (2H, m), 7.15 (3H, m), 6.39 (2H, s), 4.14 (2H, t, J=6.6 Hz), 3.69 (2H, t, J=7.0 Hz), 2.76 (2H, d, J=11.2 Hz), 2.46 (2H, d, J=10.8 Hz), 2.24 (2H, t, J=6.8 Hz), 1.61-1.78 (6H, m), 1.36-1.44 (5H, m), 1.00 (2H, m), 0.91 (3H, t, J=7.2 Hz).

Example 3

2-Butoxy-7,8-dihydro-9-(3-[4-(4-fluorobenzoyl)piperidin-1-yl]propyl)-8-oxoadenine Yield: 18%

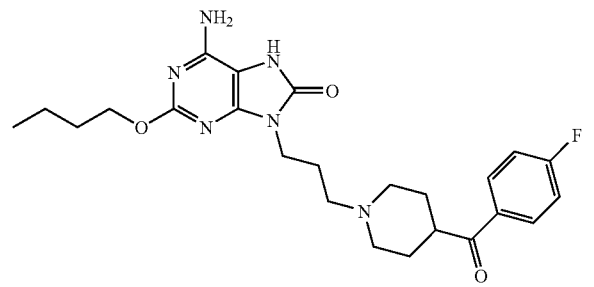

¹H NMR (DMSO-d₆) δ 9.83 (1H, s), 8.03 (2H, m), 7.35 (2H, m), 6.39 (2H, s), 4.14 (2H, t, J=6.6 Hz), 3.71 (2H, t, J=7.0 Hz), 2.86 (2H, d, J=11.2 Hz), 1.99 (2H, m), 1.80 (2H, m), 1.51-1.72 (6H, m), 1.35 (2H, m), 0.89 (3H, t, J=7.2 Hz).

Example 4

2-Butoxy-9-(3-[4-cinnamylpiperazin-1-yl]propyl)-7,8-dihydro-8-oxoadenine

Yield: 31%

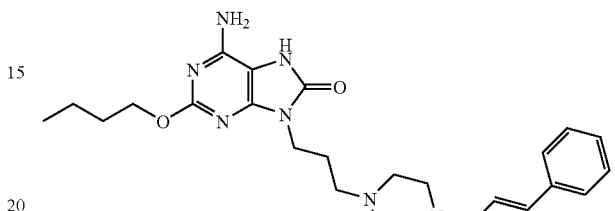

¹H NMR (DMSO-d₆) δ 9.82 (1H, s), 7.44 (2H, m), 7.32 (2H, m), 7.23 (1H, m), 6.50 (1H, d, J=16.0 Hz), 6.39 (2H, s), 6.27 (1H, m), 4.13 (2H, t, J=6.6 Hz), 3.70 (2H, t, J=6.6 Hz), 3.05 (2H, d, J=6.2 Hz), 2.32 (9H, m), 1.77 (2H, m), 1.63 (2H, m), 1.37 (2H, m), 0.89 (3H, t, J=7.2 Hz).

Example 5

9-(7-[4-(4-Acetylphenyl)piperazin-1-yl]heptyl-2-butoxy-7,8-dihydro)-8-oxoadenine Yield: 26%

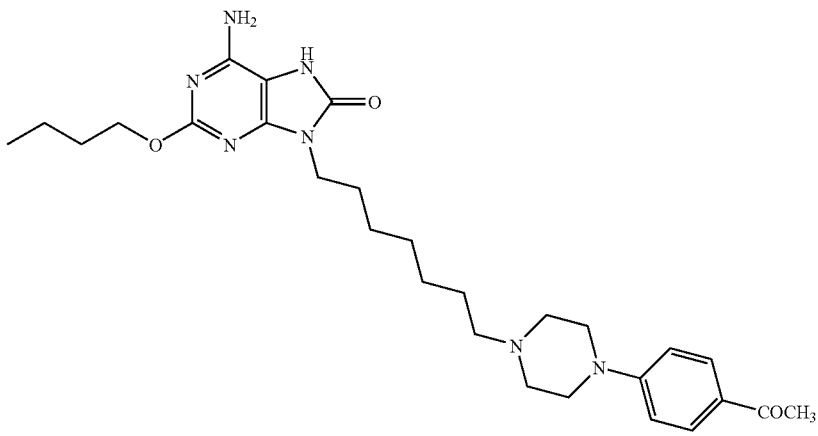

¹H NMR (DMSO-d₆) δ 9.84 (1H, s), 7.79 (2H, d, J=9.4 Hz), 6.95 (2H, d, J=9.4 Hz), 6.41 (2H, s), 4.14 (2H, t, J=6.6 Hz), 3.66 (2H, t, J=7.0 Hz), 3.30 (4H, m), 2.45 (7H, m), 2.25 (2H, m), 1.64 (4H, m), 1.25-1.41 (11H, m), 0.91 (3H, t, J=7.2 Hz).
Example 6
2-Butoxy-7,8-dihydro-9-(7-[4-(4-pyridyl)piperazin-1-yl]heptyl)-8-oxoadenine
Yield: 5%
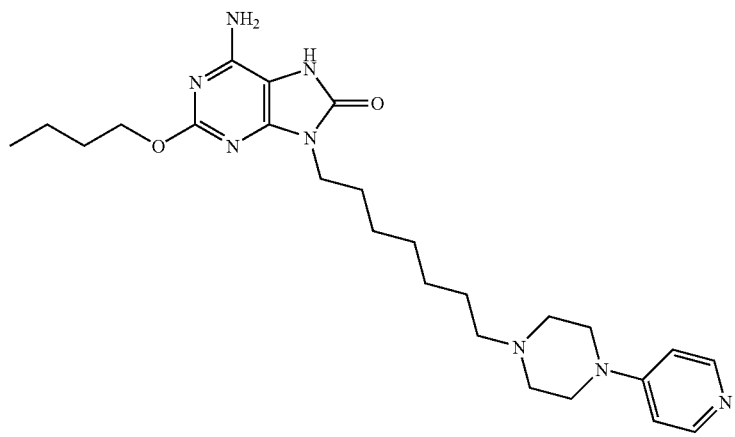
¹H NMR (DMSO-d₆) δ 9.84 (1H, s), 8.14 (2H, dd, J=1.4, 5.0 Hz), 6.80 (2H, dd, J=1.4, 5.0 Hz), 6.41 (2H, s), 4.14 (2H, t, J=6.6 Hz), 3.66 (2H, t, J=7.0 Hz), 3.27 (4H, m), 2.41 (4H, t, J=5.0 Hz), 2.26 (2H, t, J=7.2 Hz), 1.64 (4H, m), 1.25-1.41 (11H, m), 0.91 (3H, t, J=7.2 Hz).
Example 7
2-Butoxy-9-(7-[4-(4-chloro-2-methylphenoxy)piperidin-1-yl]heptyl)-7,8-dihydro-8-oxoadenine
Yield: 68%
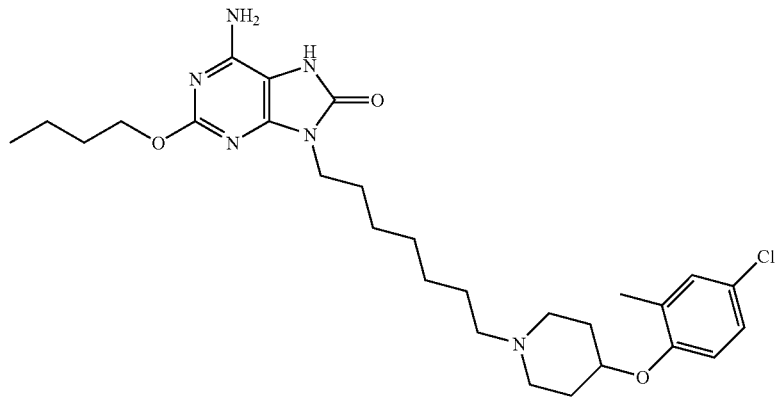
¹H NMR (DMSO-d₆) δ 9.83 (1H, s), 7.21 (1H, s), 7.15 (1H, m), 6.97 (1H, d, J=8.8 Hz), 6.40 (2H, s), 4.37 (1H, t, J=3.6 Hz), 4.14 (2H, t, J=6.6 Hz), 3.65 (2H, t, J=7.0 Hz), 2.51 (2H, m), 2.22 (4H, m), 2.13 (3H, s), 1.84 (2H, m), 1.60-1.66 (6H, m), 1.24-1.41 (10H, m), 0.91 (3H, t, J=7.2 Hz).

Example 8

2-Butoxy-7,8-dihydro-9-(7-[4-(4-methoxyphenyl)piperazin-1-yl]heptyl)-8-oxoadenine Yield: 27%

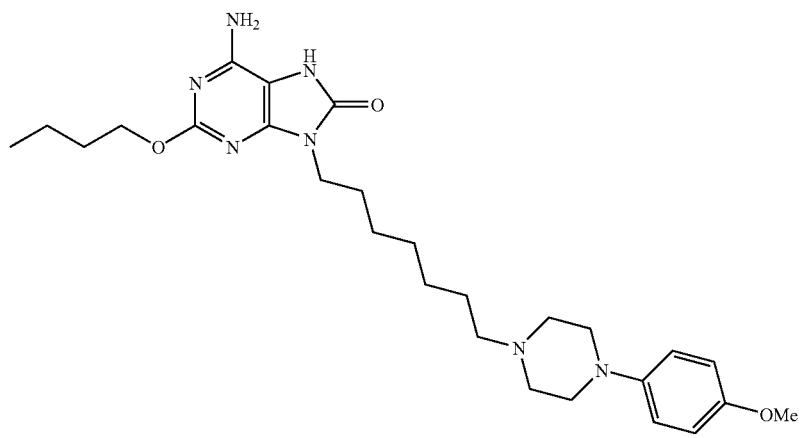

$^1$H NMR (DMSO-d$_6$) δ 9.83 (1H, s), 6.87 (2H, d, J=9.2 Hz), 6.80 (2H, d, J=9.2 Hz), 6.40 (2H, s), 4.14 (2H, t, J=6.6 Hz), 3.67 (3H, s), 3.64 (2H, m), 2.98 (4H, t, J=4.7 Hz), 2.48 (4H, m), 2.25 (2H, m), 1.63 (4H, m), 1.25-1.41 (11H, m), 0.91 (3H, t, J=7.2 Hz)

Example 9

6-Amino-9-[2-(1-benzylpiperidin-4-yl)ethyl]-2-(2-methoxyethoxy)-7,9-dihydropurin-8-one

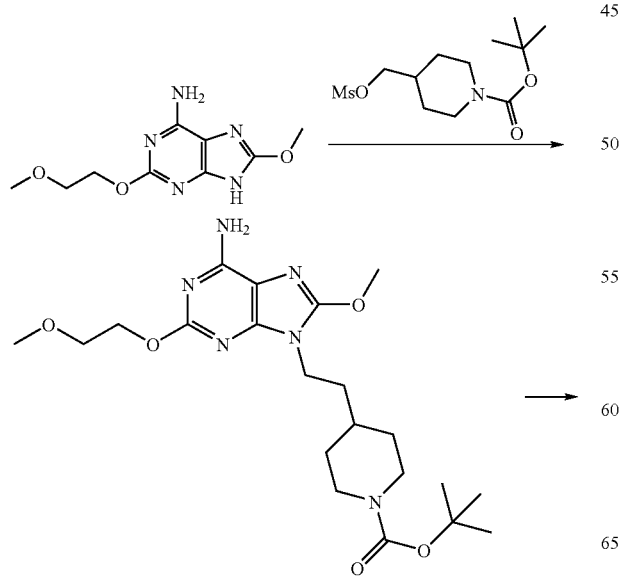

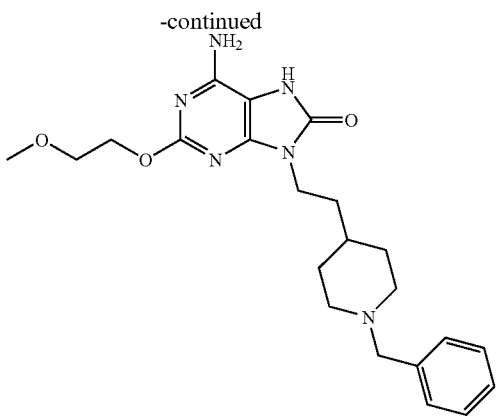

Step (i)

4-{2-[6-Amino-8-methoxy-2-(2-methoxyethoxy)purin-9-yl]ethyl}-piperidine-1-carboxylic acid tert-butyl ester 8-Methoxy-2-(2-methoxyethoxy)adenine (3.27 g, 13.7 mmol) was dissolved in DMF (75 ml), and thereto were added potassium carbonate (1.89 g, 13.7 mmol) and 4-[2-(methanesulfonyloxy)ethyl]piperidine-1-carboxylic acid tert-butyl ester (4.21 g, 13.7 mmol), and the mixture was stirred at 60° C. for 2.5 hours. The mixture was cooled to room temperature, and the carbonate salt was removed by filtration, and the filtrate was concentrated. To the residue was added water, and the mixture was extracted three times with chloroform. The resultant was dried over magnesium sulfate, and concentrated. The residue was purified by silica gel column (chloroform/methanol=200/1 to 100/1) to give the subtitle compound (3.62 g, 8.04 mmol) as a white solid. Yield: 60%.

¹H NMR (CDCl₃) δ 5.44 (2H, brs), 4.44 (2H, t, J=5.0 Hz), 4.12 (3H, s), 3.96 (2H, t, J=5.4 Hz), 3.75 (2H, t, J=5.0 Hz), 3.43 (3H, s), 2.67-2.06 (2H, m), 1.83-1.65 (6H, m), 1.45 (9H, s), 1.40-1.33 (1H, m), 1.18-1.11 (2H, m).

Step (ii)

6-Amino-9-[2-(1-benzylpiperidin-4-yl)ethyl]-2-(2-methoxyethoxy)-7,9-dihydropurin-8-one To the compound (0.26 g, 0.58 mmol) obtained in Step (i) was added trifluoroacetic acid (4 ml), and the mixture was stirred at room temperature for 20 minutes. Trifluoroacetic acid was evaporated with an evaporator, and to the resultant were added THF (10 ml), benzyl bromide (0.21 ml, 1.74 mmol) and ethyl diisopropylamine (0.75 ml, 4.35 mmol), and the mixture was stirred at room temperature for 15 hours, then stirred at 50° C. for one hour. The resultant was concentrated by an evaporator, and water was added to the residue. The mixture was extracted three times with chloroform, dried over magnesium sulfate, and concentrated. The residue was purified by silica gel column (chloroform/methanol=100/1 to 20/1). Then, methanol (1 ml) and a 4N hydrochloric acid in dioxane (1 ml) were added thereto, and the mixture was stirred at room temperature for one hour. The mixture was cooled to 0° C., and neutralized with 4% aqueous ammonia. The precipitated solid was collected by filtration, and washed with water to give the title compound (55 mg, 0.13 mmol) as a white solid. Yield: 22%.

¹H NMR (DMSO-d₆) δ 9.85 (1H, brs), 7.32-7.20 (5H, m), 6.42 (2H, brs), 4.25 (2H, t, J=4.6 Hz), 3.68 (2H, t, J=6.8 Hz), 3.59 (2H, t, J=4.7 Hz), 3.40 (2H, s), 3.27 (3H, s), 2.77-2.73 (2H, m), 1.86-1.80 (2H, m), 1.71-1.67 (2H, m), 1.58-1.54 (2H, m), 1.20-1.10 (3H, m).

Example 10

6-Amino-9-{2-[1-(4-dimethylaminomethylbenzyl)piperidin-4-yl]ethyl}-2-(2-methoxyethoxy)-7,9-dihydropurin-8-one

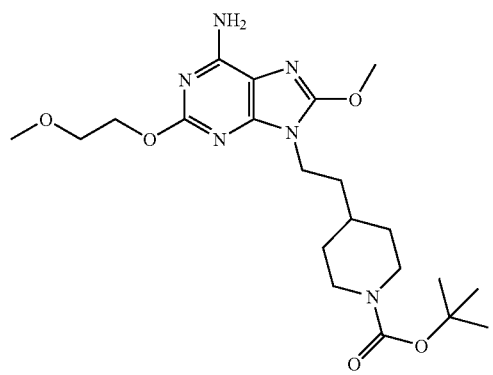

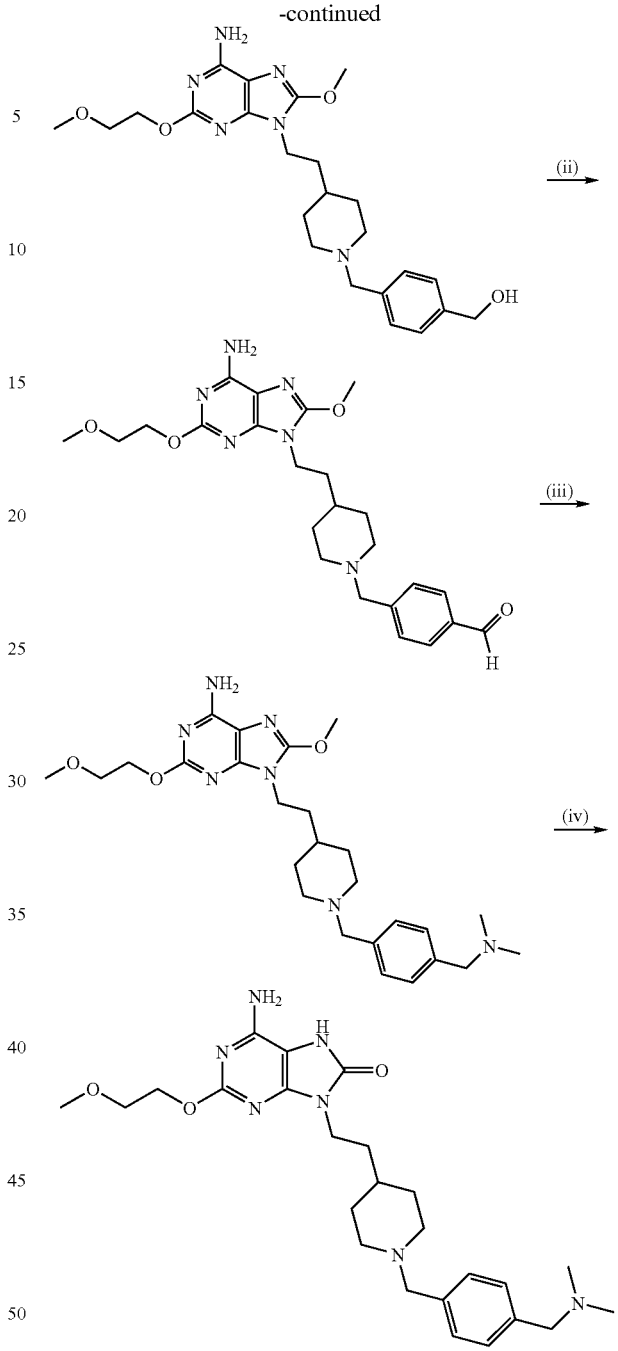

Step (i)

[4-(4-{2-[6-Amino-8-methoxy-2-(2-methoxyethoxy)purin-9-yl]ethyl}-piperidin-1-ylmethyl)phenyl]methanol To the compound (0.84 g, 1.86 mmol) obtained in Example 9, Step (i) was added trifluoroacetic acid (12 ml), and the mixture was stirred at room temperature for 20 minutes. Trifluoroacetic acid was evaporated by an evaporator, and DMF (15 ml), 4-(chloromethyl)benzyl alcohol (0.32 g, 2.04 mmol), and potassium carbonate (1.28 g, 9.30 mmol) were added thereto, and the mixture was stirred at room temperature for 18 hours. The carbonate was removed by filtration, and the filtrate was concentrated. Water was added to the residue, and the mixture was extracted three times with chloroform/ethanol=3/1. The resultant was dried over magnesium sulfate, concentrated, and purified by silica gel column (chloroform/methanol=20/1) to give the subtitle compound (0.52 g, 1.11 mmol) as a white solid. Yield: 60%.

$^1$H NMR (CDCl$_3$) δ 7.24 (4H, brs), 5.13 (2H, brs), 4.62 (2H, d, J=4.8 Hz), 4.34 (2H, t, J=5.0 Hz), 4.00 (3H, s), 3.87 (2H, t, J=7.1 Hz), 3.67 (2H, t, J=5.0 Hz), 3.41 (2H, s), 3.35 (3H, s), 2.83-2.76 (2H, m), 2.07 (1H, t, J=4.8 Hz), 1.87-1.80 (2H, m), 1.68-1.55 (4H, m), 1.26-1.10 (3H, m).

Step (ii)

4-(4-{2-[6-Amino-8-methoxy-2-(2-methoxyethoxy)purin-9-yl]ethyl}-piperidin-1-ylmethyl)benzaldehyde The compound (0.52 g, 1.10 mmol) obtained in Step (i) and manganese dioxide (0.95 g, 11.0 mmol) were added to chloroform (20 ml), and the mixture was stirred at room temperature for 15 hours. The mixture was filtered, and the filtrate was concentrated. The residue was purified by silica gel column (chloroform/methanol=100/1 to 50/1) to give the subtitle compound (0.47 g, 1.00 mmol) as a white solid. Yield: 92%.

$^1$H NMR (DMSO-d$_6$) δ 9.97 (1H, s), 7.85 (2H, d, J=8.0 Hz), 7.50 (2H, d, J=8.0 Hz), 6.81 (2H, brs), 4.26 (2H, t, J=4.7 Hz), 4.04 (3H, s), 3.86 (2H, t, J=6.8 Hz), 3.59 (2H, t, J=4.7 Hz), 3.51 (2H, s), 3.27 (3H, s), 2.77-2.71 (2H, m), 1.91-1.82 (2H, m), 1.71-1.66 (2H, m), 1.63-1.57 (2H, m), 1.20-1.10 (3H, m).

Step (iii)

9-{2-[1-(4-Dimethylaminomethylbenzyl)piperidin-4-yl]ethyl}-8-methoxy-2-(2-methoxyethoxy)-9H-purin-6-ylamine The compound (0.31 g, 1.66 mmol) obtained in Step (ii) was dissolved in THF (10 ml), and thereto were added at 0° C. dimethylamine (2M THF solution, 2.62 ml, 5.24 mmol) and sodium triacetoxy borohydride (0.56 g, 2.62 mmol), and the mixture was stirred at room temperature for 20 hours. The mixture was cooled to 0° C., and thereto was added a saturated aqueous sodium hydrogencarbonate solution, and the mixture was extracted three times with chloroform/ethanol=3/1. The extract was dried over magnesium sulfate, concentrated, and purified by silica gel column (chloroform/methanol/28% aqueous ammonia=100/5/0 to 100/5/1) to give the title compound (0.28 g, 0.57 mmol) as a white solid. Yield: 87%.

$^1$H NMR (DMSO-d$_6$) δ 7.20 (4H, brs), 6.81 (2H, brs), 4.26 (2H, t, J=4.8 Hz), 4.04 (3H, s), 3.86 (2H, t, J=6.9 Hz), 3.59 (2H, t, J=4.8 Hz), 3.37 (2H, s), 3.33 (2H, s), 3.27 (3H, s), 2.77-2.70 (2H, m), 2.11 (6H, s), 1.85-1.76 (2H, m), 1.71-1.65 (2H, m), 1.62-1.56 (2H, m), 1.15-1.10 (3H, m).

Step (iv)

6-Amino-9-{2-[1-(4-dimethylaminomethylbenzyl)piperidin-4-yl]ethyl}-2-(2-methoxyethoxy)-7,9-dihydropurin-8-one To the compound (0.28 g, 0.57 mmol) obtained in Step (iii) were added methanol (3 ml) and a 4N hydrochloric acid in dioxane (3 ml), and the mixture was stirred at room temperature for one hour. The mixture was cooled to 0° C., and neutralized with 4% aqueous ammonia. The precipitated solid was collected by filtration, and washed with water to give the title compound (0.18 g, 0.19 mmol) as a white solid. Yield: 65%.

$^1$H NMR (DMSO-d$_6$) δ 9.85 (1H, brs), 7.20 (4H, brs), 6.43 (2H, brs), 4.25 (2H, t, J=4.8 Hz), 3.68 (2H, t, J=6.9 Hz), 3.59 (2H, t, J=4.8 Hz), 3.38 (2H, s), 3.33 (2H, s), 3.27 (3H, s), 2.77-2.70 (2H, m), 2.11 (6H, s), 1.86-1.78 (2H, m), 1.72-1.65 (2H, m), 1.60-1.53 (2H, m), 1.15-1.10 (3H, m).

Example 11

Human TLR7 Reporter Assay

Human TLR7 or rat TLR7 plasmid and a reporter plasmid (NF-kB-SEAP) stably-induced HEK293 cells were suspended in DMEM media (10% FBS, 1% NEAA, 10 μg/mL blastocidin S HCl, 100 ug/mL Zeocin), and the suspension was seeded on a 96-well plate in an amount of 90 μl/well (hTLR7/seap-293: 20000 cells/well, rTLR7/seap-293: 25000 cells/well).

To the cells seeded on the 96-well plate was added a test compound wherein DMSO stock solution (2 μl) was hundred-fold diluted with medium (200 μl) in an amount of 10 μl/well (final concentration; 1 nM-10 μM, common ratio 3). The mixture was stirred by tapping in the side of the plate, and then incubated for 20 hours in a CO$_2$ incubator. To the cells stimulated by a test compound was added a substrate for reporter assay (substrate for SEAP, pNPP) in an amount of 50 μl/well. Ten minutes after the addition of the substrate, a quenching solution (4N NaOH) was added in an amount of 50 μl/well, and the enzymatic reaction was quenched. Top seal A was attached on the plate, and the absorbance was measured by microplate reader (405 nm).

Human TLR7 binding activity (pEC50) of each compound is shown in Table 1.

TABLE 1

| Compound | pEC50 |
|---|---|
| Example 4 | 6.1 |
| Example 5 | 6.8 |
| Example 6 | 7.5 |
| Example 7 | 6.2 |
| Example 8 | 6.6 |

Example 12

9-[1-(3-{N-benzyl-N-methylamino}propyl)piperidin-4-yl]methyl-2-butoxy-7,8-dihydro-8-oxoadenine

This compound can be prepared in a similar manner to Example 9.

Example 13

2-Butoxy-7,8-dihydro-9-{1-[3-(N-2-phenoxyethyl-N-methylamino)-propyl]piperidin-4-ylmethyl}-8-oxoadenine

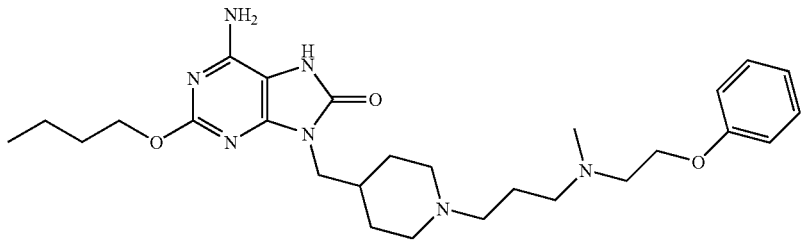

This compound can be prepared in a similar manner to Example 9.

Example 14

2-Butoxy-7,8-dihydro-9-[7-(4-{2-[N-methyl-N-benzyl]aminomethyl}-piperazin-1-yl)heptyl]-8-oxoadenine

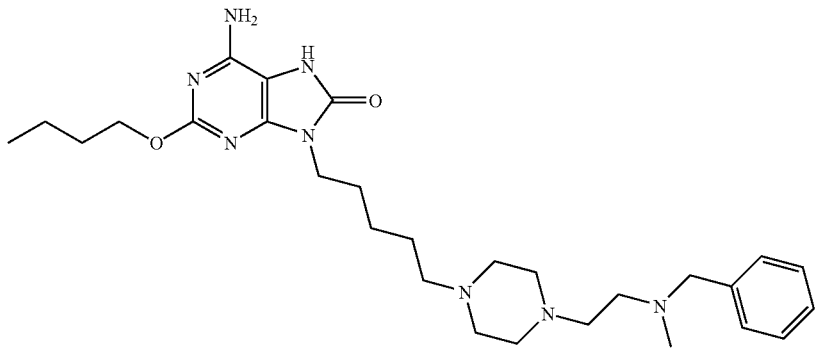

This compound can be prepared by the same method as Example 1.

Example 15

2-Butoxy-7,8-dihydro-9-[7-(4-{2-[N-methyl-N-benzyl]aminomethyl}-piperazin-1-yl)heptyl]-8-oxoadenine

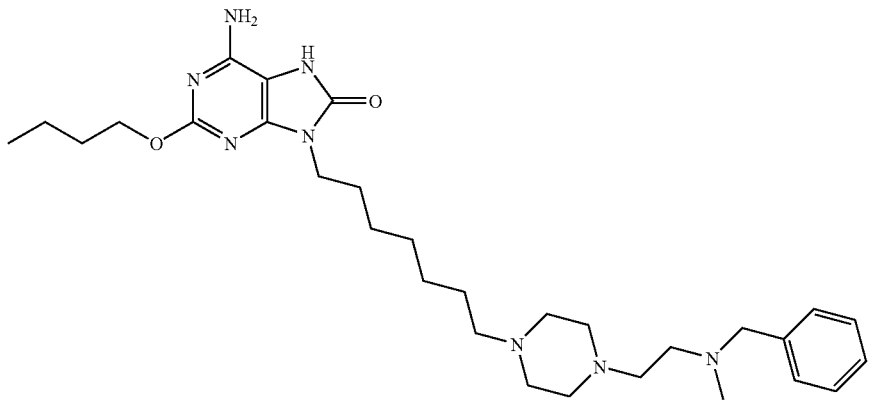

This compound can be prepared by the same method as Example 1.

Example 16

2-Butoxy-7,8-dihydro-9-(7-{4-[2-phenoxyethyl]piperazin-1-yl}heptyl)-8-oxoadenine

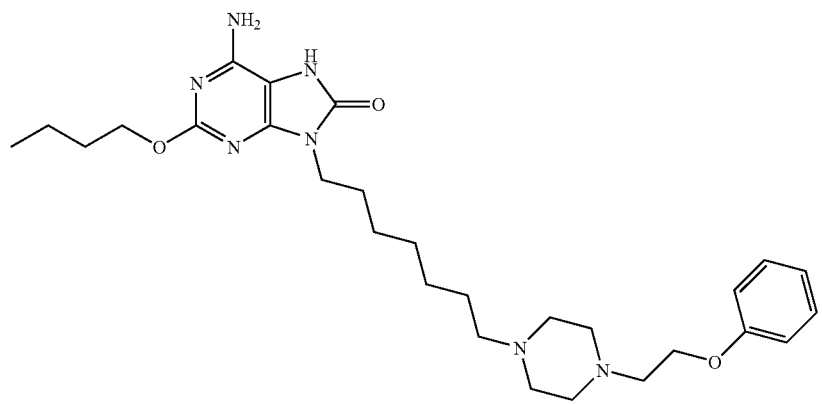

This compound can be prepared by the same method as Example 1.

Example 17

9-(3-[2-benzyl-4-methyl-piperazin-1-yl]heptyl)-2-butoxy-7,8-dihydro-8-oxoadenine

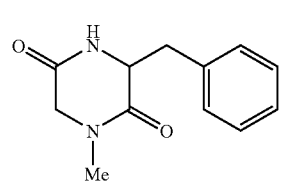

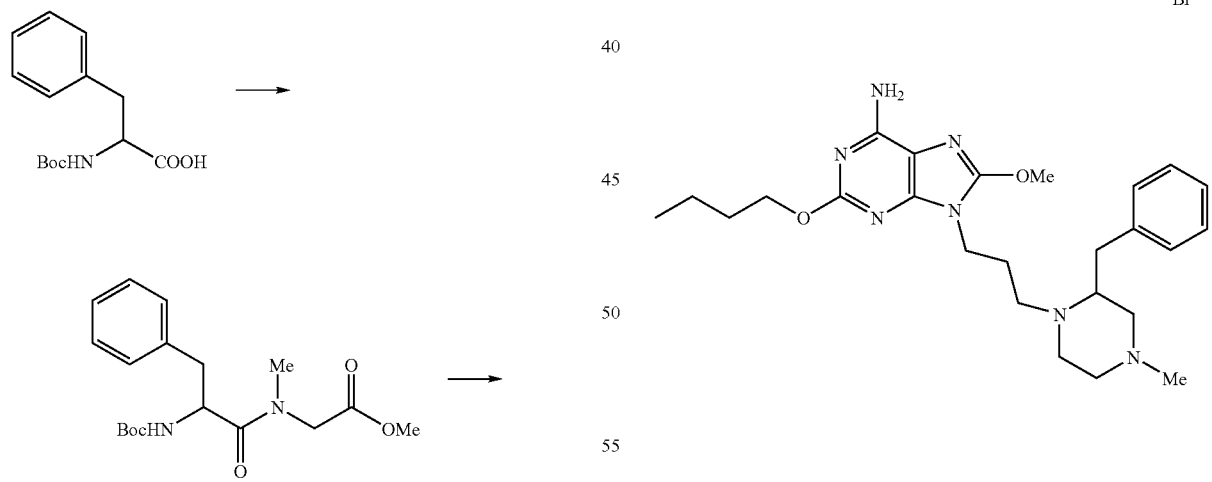

Step (i)

Methyl N-(tert-butoxycarbonyl)-phenylalanyl-N-methylglycinate

N-(tert-Butoxycarbonyl)-phenylalanine (4.85 g, 15 mmol) was condensed with N-methylglycine methyl ester hydrochloride in DMF in the presence of triethylamine, HOBt and WSC.

Step (ii)

2-Benzyl-4-methyl-3,6-dioxopiperazine

The compound obtained in Step (i) was treated with trifluoroacetic acid (30 ml), and then the resultant was heated under reflux in methanol in the presence of triethylamine to give the subtitle compound.

Step (iii)

tert-Butyl 2-benzyl-4-methylpiperazine-1-carboxylate

The compound obtained in Step (ii) was subjected to reduction with lithium aluminum hydride in THF. Then, the resultant was subjected to Boc-introducing reaction with di-tert-butyl carbonate to give the subtitle compound.

Step (vi)

The compound obtained in Step (iii) was reacted with the compound obtained in Example 1, Step (i) in the presence of potassium iodide (166 mg, 1 mmol) and potassium carbonate (207 mg, 1.5 mmol) in DMF to give the title compound.

Example 18

9-(3-[3-Benzyl-4-methyl-piperazin-1-yl]heptyl)-2-butoxy-7,8-dihydro-8-oxoadenine

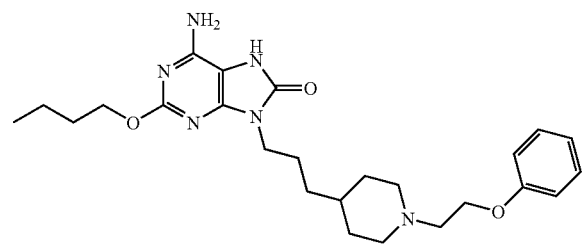

The above compound can be prepared in a similar manner to Example 17.

Example 19

2-Butoxy-7,8-dihydro-9-(3-{1-(2-phenoxyethyl)piperidin-4-yl}propyl)-8-oxoadenine

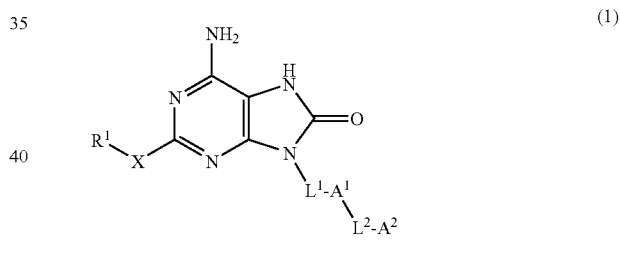

This compound can be prepared in a similar manner to Example 9.

Example 20

2-Butoxy-7,8-dihydro-9-(3-{1-phenoxyethylpiperidin-4-yl}propyl)-8-oxoadenine

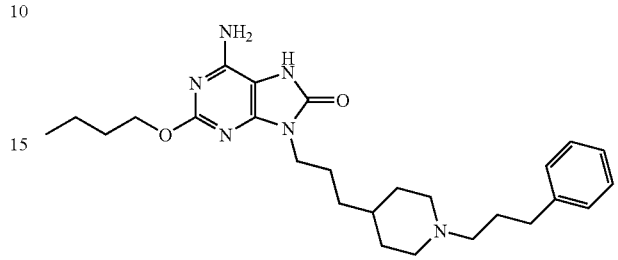

This compound can be prepared in a similar manner to Example 9.

INDUSTRIAL APPLICABILITY

By the present invention, it has become possible to provide a novel adenine compound being useful as a therapeutic or preventive agent for allergic diseases, viral diseases, cancers, etc.

The invention claimed is:
1. An adenine compound of the formula (1):

[wherein $R^1$ is a halogen atom, a substituted or unsubstituted $C_{1-12}$ alkyl group, a substituted or unsubstituted $C_{2-10}$ alkenyl group, a substituted or unsubstituted $C_{2-10}$ alkynyl group, a substituted or unsubstituted $C_{3-8}$ cycloalkyl group, a substituted or unsubstituted 6- to 10-membered aryl group, or a substituted or unsubstituted 5- to 10-membered heteroaryl group, X is an oxygen atom, a sulfur atom, $NR^2$ ($R^2$ is a hydrogen atom or a $C_{1-6}$ alkyl group), SO, $SO_2$ or a single bond (when $R^1$ is a halogen atom, then X is a single bond), $A^1$ is a 4- to 8-membered substituted or unsubstituted, saturated nitrogen-containing heterocycle or an unsaturated non-aromatic nitrogen-containing heterocycle, said heterocycle containing 1 to 2 heteroatom(s) selected from 1 to 2 nitrogen atom(s), 0 to 1 oxygen atom and 0 to 1 sulfur atom, $A^2$ is a substituted or unsubstituted 6- to 10-membered aryl group or a substituted or unsubstituted 5- to 10-membered heteroaryl group, $L^1$ and $L^2$ are independently a $C_{1-12}$ alkylene group, a $C2$-$12$ alkenylene group, or a single bond, and any 1 to 3 methylene group(s) in said alkylene group or alkenylene group may be replaced by an oxygen atom, a sulfur atom, NR³ (R³ is a hydrogen atom or a C₁₋₆ alkyl group), SO, SO₂, or a carbonyl group], or a pharmaceutically acceptable salt thereof.

2. The adenine compound according to claim 1, wherein when the alkyl group, the alkenyl group and the alkynyl group for R¹ are substituted, those groups are substituted by 1 or more groups independently selected from the group consisting of (a), (b) and (c):

(a) a halogen atom, a hydroxy group, a carboxyl group, a mercapto group, an oxo group, a C₁₋₆ haloalkyl group and a C₁₋₆ haloalkoxy group;

(b) a C₁₋₆ alkoxy group, a C₂₋₆ alkylcarbonyl group, a C₂₋₆ alkoxycarbonyl group, a C₁₋₆ alkylsulfonyl group, a C₁₋₆ alkylsulfinyl group, a C₂₋₆ alkylcarbonyloxy group and a C₁₋₆ alkylthio group, wherein a group (b) may optionally and independently be substituted by 1 or more groups selected from a halogen atom, a hydroxy group, a carboxyl group, a C₁₋₆ alkoxy group, a C₂₋₆ alkoxycarbonyl group, an amino group being optionally substituted by one or two of the same or different C₁₋₆ alkyl group(s), a carbamoyl group being optionally substituted by one or two of the same or different C₁₋₆ alkyl group(s), a sulfamoyl group being optionally substituted by one or two of the same or different C₁₋₆ alkyl group(s), and a C₁₋₆ alkylsulfonyl group);

(c) an amino group that may optionally be substituted by 1 or 2 groups selected from the group consisting of (k), (l) and (m), a carbamoyl group that may optionally be substituted by 1 or 2 groups selected from the group consisting of (k), (l) and (m) and a sulfamoyl group that may optionally be substituted by 1 or 2 groups selected from the group consisting of (k), (l) and (m), a 3- to 8-membered cycloalkyl group that may optionally be substituted by 1 or more groups selected from the group consisting of (d), (e) and (f), a 3- to 8-membered cycloalkoxy group that may optionally be substituted by 1 or more groups selected from the group consisting of (d), (e) and (f) and a 4- to 8-membered saturated heterocyclic group that may optionally be substituted by 1 or more groups selected from the group consisting of (d), (e) and (f), and a 6- to 10-membered aryl group that may optionally be substituted by 1 or more groups selected from the group consisting of (g), (h), (i) and (j), a 5- to 10-membered heteroaryl group that may optionally be substituted by 1 or more groups selected from the group consisting of (g), (h), (i) and (j), a 6- to 10-membered aryloxy group that may optionally be substituted by 1 or more groups selected from the group consisting of (g), (h), (i) and (j) and a 5- to 10-membered heteroaryloxy group that may optionally be substituted by 1 or more groups selected from the group consisting of (g), (h), (i) and (j), wherein when the cycloalkyl group for R¹ is substituted, it is substituted by one or more groups selected from the group consisting of (d), (e) and (f):

(d) a halogen atom, a hydroxy group, a carboxyl group, a mercapto group, an oxo group, a cyano group, a nitro group, a C₁₋₆ haloalkyl group, and a C₁₋₆ haloalkoxy group;

(e) a C₁₋₆ alkyl group, a C₁₋₆ alkoxy group, a C₂₋₆ alkenyl group, a C₂₋₆ alkynyl group, a C₂₋₆ alkylcarbonyl group, a C₂₋₆ alkoxycarbonyl group, a C₁₋₆ alkylsulfonyl group and a C₁₋₆ alkylthio group, wherein a group (e) may optionally and independently be substituted by 1 or more groups selected from a halogen atom, a hydroxy group, a carboxyl group, a C₁₋₆ alkoxy group, a C₂₋₆ alkoxycarbonyl group, an amino group being optionally substituted by one or two of the same or different C₁₋₆ alkyl group(s), a carbamoyl group being optionally substituted by one or two of the same or different C₁₋₆ alkyl group(s), a sulfamoyl group being optionally substituted by one or two of the same or different of C₁₋₆ alkyl group(s), and a C₁₋₆ alkylsulfonyl group;

(f) an amino group that may optionally be substituted by 1 or 2 groups selected from the group consisting of (k), (l) and (m), a carbamoyl group that may optionally be substituted by 1 or 2 groups selected from the group consisting of (k), (l) and (m) and a sulfamoyl group that may optionally be substituted by 1 to 2 groups selected from the group consisting of (k), (l) and (m), a 6- to 10-membered aryl group that may optionally be substituted by one or more groups selected from the group consisting of (g), (h), (i) and (j), and a 5- to 10-membered heteroaryl group that may optionally be substituted by 1 or more groups selected from the group consisting of (g), (h), (i) and (j);

wherein when the aryl group and heteroaryl group for R¹ are substituted, those groups are substituted by one or more groups selected from the group consisting of (g), (h), (i) and (j):

(g) a halogen atom, a hydroxy group, a mercapto group, a cyano group, a nitro group, a C₁₋₆ haloalkyl group, and a C₁₋₆ haloalkoxy group;

(h) a C₁₋₆ alkyl group, a C₁₋₆ alkoxy group, a C₂₋₆ alkenyl group, a C₂₋₆ alkynyl group, a C₂₋₆ alkylcarbonyl group, a C₂₋₆ alkoxy-carbonyl group, and a C₁₋₆ alkylthio group, wherein a group (h) may optionally and independently be substituted by 1 or more groups selected from a halogen atom, a hydroxy group, a carboxyl group, a C₁₋₆ alkoxy group, a C₂₋₆ alkoxycarbonyl group, an amino group being optionally substituted by one or two of the same or different C₁₋₆ alkyl group(s), a carbamoyl group being optionally substituted by one or two of the same or different C₁₋₆ alkyl group(s), a sulfamoyl group being optionally substituted by one or two of the same or different C₁₋₆ alkyl group(s), and a C₁₋₆ alkylsulfonyl group;

(i) a 3- to 8-membered cycloalkyl group and a 4- to 8-membered saturated heterocyclic group, wherein a group (i) may optionally and independently be substituted by one or more groups selected from a halogen atom, a hydroxy group, a carboxyl group, a C₁₋₆ alkyl group and a C₁₋₆ alkoxy group;

(j) an amino group that may optionally be substituted by one or two groups selected from the group consisting of (k), (l) and (m), a carbamoyl group that may optionally be substituted by one or two groups selected from the group consisting of (k), (l) and (m), and a sulfamoyl group that may optionally be substituted by one or two groups selected from the group consisting of (k), (l) and (m);

(k) a C₁₋₆ alkyl group, a C₂₋₆ alkenyl group, a C₂₋₆ alkynyl group, a C₂₋₆ alkylcarbonyl group, a C₂₋₆ alkoxycarbonyl group, a C₁₋₆ alkylsulfonyl group, a C₁₋₆ alkylsulfinyl group, a 3- to 8-membered cycloalkyl group, a 3- to 8-membered cycloalkylcarbonyl group, a 3- to 8-membered cycloalkoxycarbonyl group, a 3- to 8-membered cycloalkylsulfonyl group, and a 3- to 8-membered cycloalkylsulfinyl group, wherein a group (k) may optionally be substituted by one or more groups selected from a halogen atom, a hydroxy group, a carboxyl group, a C₁₋₆ alkoxy group and a C₂₋₆ alkoxycarbonyl group;

(l) a 6- to 10-membered aryl group, a 6- to 10-membered arylcarbonyl group, a 6- to 10-membered aryloxycarbonyl group, a 6- to 10-membered arylsulfonyl group, a 6- to 10-membered arylsulfinyl group, a 5- to 10-membered heteroaryl group, a 5- to 10-membered heteroarylcarbonyl group, a 5- to 10-membered heteroaryloxycarbonyl group, a 5- to 10-membered heteroarylsulfonyl group, and a 5- to 10-membered heteroarylsulfinyl group, wherein a group (l) may optionally be substituted by a halogen atom, a hydroxy group, a mercapto group, a cyano group, a nitro group, a carboxyl group, a $C_{1-6}$ alkyl group, a $C_{1-6}$ alkoxy group, a $C_{2-6}$ alkoxycarbonyl group, or a $C_{1-6}$ alkylthio group;

(m) a group where two substituents combine together with a nitrogen atom to form a 4- to 8-membered nitrogen-containing saturated heterocycle containing 1 to 4 heteroatom(s) selected from 1 to 3 nitrogen atom(s), 0 to 1 oxygen atom, and 0 to 1 sulfur atom wherein said nitrogen-containing saturated heterocycle may optionally be substituted on any carbon atoms or nitrogen atoms by one or more of the same or different groups selected from a halogen atom, a hydroxy group, a carboxyl group, a $C_{1-6}$ alkyl group, a $C_{1-6}$ alkoxy group, a $C_{2-6}$ alkoxycarbonyl group and a $C_{2-6}$ alkylcarbonyl group, wherein when the 4- to 8-membered nitrogen-containing heterocycle for $A^1$ is substituted, it is substituted by one or more group(s) independently selected from the group consisting of a halogen atom, a hydroxy group, an oxo group, a $C_{1-6}$ alkyl group, a $C_{1-6}$ alkoxy group, a $C_{2-6}$ alkylcarbonyl group, and a $C_{2-6}$ alkoxycarbonyl group;

wherein when the 6- to 10-membered aryl group and the 5- to 10-membered heteroaryl group for $A^2$ are substituted, they are substituted by one or more group(s) independently selected from the group consisting of (g'), (h') and (i');

(g') a halogen atom, a hydroxy group, a mercapto group, a cyano group, a nitro group, a $C_{1-6}$ haloalkyl group, and a $C_{1-6}$ haloalkoxy group;

(h') a $C_{1-6}$ alkyl group, a $C_{1-6}$ alkoxy group, a $C_{2-6}$ alkylcarbonyl group, a $C_{1-6}$ alkylsulfonyl group, and a $C_{1-6}$ alkylthio group, wherein a group (h') may optionally be substituted by one or more of the same or different groups selected from a halogen atom, a hydroxy group, a $C_{1-6}$ alkoxy group, a $C_{1-6}$ alkylsulfonyl group, an amino group, a carbamoyl group and a sulfamoyl group, wherein the above amino, carbamoyl and sulfamoyl groups may optionally be substituted by one or two groups selected from the group consisting of (j') and (k');

(i') an amino group, a carbamoyl group, and a sulfamoyl group, wherein a group (i') may optionally be substituted by one or two groups selected from the group consisting of (j') and (k');

(j') a $C_{1-6}$ alkyl group, a $C_{2-6}$ alkylcarbonyl group, a $C_{1-6}$ alkylsulfonyl group, a $C_{1-6}$ alkylsulfinyl group, a 3- to 8-membered cycloalkyl group, a 3- to 8-membered cycloalkylcarbonyl group, a 3- to 8-membered cycloalkoxycarbonyl group, a 3- to 8-membered cycloalkylsulfonyl group, and a 3- to 8-membered cycloalkylsulfinyl group, wherein a group (j') may optionally and independently be substituted by one or more groups selected from the group consisting of a halogen atom, a hydroxy group, a $C_{1-6}$ alkyl group and a $C_{1-6}$ alkoxy group;

(k') a group where two substituents combine together with a nitrogen atom to form a 4- to 8-membered nitrogen-containing saturated heterocycle containing 1 to 4 heteroatom(s) selected from 1 to 3 nitrogen atom(s), 0 to 1 oxygen atom, and 0 to 1 sulfur atom wherein said nitrogen-containing saturated heterocycle may optionally be substituted on any carbon atoms or nitrogen atoms by one or more groups selected from the group consisting of a halogen atom, a hydroxy group, a $C_{1-6}$ alkyl group, a $C_{1-6}$ alkoxy group and a $C_{2-6}$ alkylcarbonyl; or a pharmaceutically acceptable salt thereof.

3. The adenine compound according to claim 1, or a pharmaceutically acceptable salt thereof, wherein in the formula (1), $A^1$ is pyrrolidine, piperidine, azetidine, piperazine, morpholine, thiomorpholine, thiomorpholin-1-oxide, or thiomorpholine-1,1-dioxide, these groups being either substituted or unsubstituted.

4. The adenine compound according to claim 1, or a pharmaceutically acceptable salt thereof, wherein in the formula (1), $A^2$ is a phenyl group, a pyridyl group, a furyl group, an imidazolyl group or a thienyl group, these groups being either substituted or unsubstituted.

5. The adenine compound according to claim 1, or a pharmaceutically acceptable salt thereof, wherein in the formula (1), $A^1$ is pyrrolidine, piperidine or piperazine, and $A^2$ is a substituted or unsubstituted phenyl group or a substituted or unsubstituted pyridyl group.

6. The adenine compound according to claim 1, or a pharmaceutically acceptable salt thereof, wherein in the formula (1), $L^1$ is a group of the following formula:

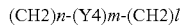

(CH2)*n*-(Y4)*m*-(CH2)*l*

[in which n and l are independently an integer of 0 to 5, and m is 0 or 1, provided that when m is 1, then n is 2 or more, and $Y^4$ is an oxygen atom or $NR^3$ ($R^3$ is a hydrogen atom or a $C_{1-6}$ alkyl group)], $L^2$ is a single bond, an oxygen atom, a carbonyl group, C1-10 straight chain or branched chain alkylene, a $C_{2-10}$ straight chain or branched chain alkenylene, or a group of the following formula:

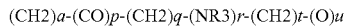

(CH2)*a*-(CO)*p*-(CH2)*q*-(NR3)*r*-(CH2)*t*-(O)*u*

[in which $R^3$ is a hydrogen atom or a $C_{1-6}$ alkyl group, a, t and q are independently an integer of 0 to 4, p, r and u are independently 0 or 1, provided that when r and u are 1, then t is 2 or more.

7. The adenine compound according to claim 1, or a pharmaceutically acceptable salt thereof, wherein in the formula (1), $L^1$ is a C2-8 straight chain or branched chain alkylene, and $L^2$ is a single bond, an oxygen atom, a carbonyl group, a $C_{1-6}$ straight chain or branched chain alkylene or a $C_{2-6}$ straight chain or branched chain alkenylene.

8. The adenine compound according to claim 1, or a pharmaceutically acceptable salt thereof, wherein $R^3$ is a hydrogen atom or a $C_{1-4}$ alkyl group.

9. The adenine compound according to claim 1 or a pharmaceutically acceptable salt thereof, wherein the compound is selected from the group consisting of:

2-butoxy-7,8-dihydro-9-(3-[4-(4-methylbenzyl)piperazin-1-yl]-propyl)-8-oxoadenine, 9-(3-[4-benzylpiperidin-1-yl]propyl)-2-butoxy-7,8-dihydro-8-oxoadenine, 2-butoxy-7,8-dihydro-9-(3-[4-(4-fluorobenzoyl)piperidine-1-yl]-propyl)-8-oxoadenine, 2-butoxy-9-(3-[4-cinnamylpiperazin-1-yl]propyl)-7,8-dihydro-8-oxoadenine, 9-(7-[4-(4-acetylphenyl)piperazin-1-yl]heptyl)-2-butoxy-7,8-dihydro-8-oxoadenine, 2-butoxy-7,8-dihydro-9-(7-[4-(4-pyridyl)piperazin-1-yl] heptyl)-8-oxoadenine, 2-butoxy-9-(7-[4-(4-chloro-2-methylphenoxy)piperazin-1-yl]-heptyl)-7,8-dihydro-8-oxoadenine,
2-butoxy-7,8-dihydro-9-(7-[4-(4-methoxyphenyl)piperazin-1-yl]-heptyl)-8-oxoadenine,
6-amino-9-[2-(1-benzylpiperidin-4-yl)ethyl]-2-(2-methoxyethoxy)-7,9-dihydropurin-8-one,
6-amino-9-{2-[1-(4-dimethylaminomethylbenzyl)piperidin-4-yl]-ethyl}-2-(2-methoxyethoxy)-7,9-dihydropurin-8-one,
9-[1-(3-{N-benzyl,N-methylamino}propyl)piperidin-4-yl]methyl-2-butoxy-7,8-dihydro-8-oxoadenine,
2-butoxy-7,8-dihydro-9-{1-[3-(N-2-phenoxyethyl-N-methyl-amino)-propyl]-piperidin-4-ylmethyl}-8-oxoadenine,
2-butoxy-7,8-dihydro-9-[7-(4-{2-[N-methyl-N-benzyl]aminoethyl}-piperazin-1-yl)pentyl]-8-oxoadenine,
2-butoxy-7,8-dihydro-9-[7-(4-{2-[N-methyl-N-benzyl]aminoethyl}-piperazin-1-yl)heptyl]-8-oxoadenine,
2-butoxy-7,8-dihydro-9-(7-{4-[2-phenoxyethyl]piperazin-1-yl}-heptyl)-8-oxoadenine,
9-(3-[2-benzyl-4-methyl-piperazin-1-yl]propyl)-2-butoxy-7,8-dihydro-8-oxoadenine,
9-(3-[3-benzyl-4-methyl-piperazin-1-yl]propyl)-2-butoxy-7,8-dihydro-8-oxoadenine,
2-butoxy-7,8-dihydro-9-(3-{1-(2-phenoxyethyl)piperidin-4-yl}-propyl)-8-oxoadenine, and
2-butoxy-7,8-dihydro-9-[3-{1-(3-phenylpropyl)piperidin}-4-yl]-propyl)-8-oxoadenine.

10. A pharmaceutical composition comprising as an active ingredient an adenine compound as set forth in claim 1, or a pharmaceutically acceptable salt thereof, and a pharmaceutically acceptable carrier.

* * * * *